US012725682B2

(12) United States Patent
Heilbroner et al.

(10) Patent No.: US 12,725,682 B2
(45) Date of Patent: Sep. 1, 2026

(54) SYSTEMS, METHODS, AND ARTICLES FOR IMPUTING DIRECTED TEMPORAL MEASUREMENTS

(71) Applicant: Tempus AI, Inc., Chicago, IL (US)

(72) Inventors: Samuel Peter Heilbroner, San Francisco, CA (US); Riccardo Miotto, New York, NY (US); Dany Michael Haddad, Austin, TX (US)

(73) Assignee: Tempus Labs, Inc., Chicago, IL (US)

( * ) Notice: Subject to any disclaimer, the term of this patent is extended or adjusted under 35 U.S.C. 154(b) by 47 days.

(21) Appl. No.: 18/450,160

(22) Filed: Aug. 15, 2023

(65) Prior Publication Data

US 2025/0061989 A1 Feb. 20, 2025

(51) Int. Cl.
*G16H 10/60* (2018.01)

(52) U.S. Cl.
CPC .................................. *G16H 10/60* (2018.01)

(58) Field of Classification Search
CPC .................................................... G16H 10/60
See application file for complete search history.

(56) References Cited

U.S. PATENT DOCUMENTS 11,177,041 B1 * 11/2021 Sutton .................... G16H 50/30
11,475,988 B1 * 10/2022 Burkart .................. G16H 20/60
2008/0133275 A1 * 6/2008 Haug ..................... G16H 50/20 705/3
2011/0105852 A1 * 5/2011 Morris .................. G06Q 10/10 600/300
2017/0134493 A1 * 5/2017 Chang ................. H04L 67/1025
2019/0361934 A1 * 11/2019 Rogynskyy ............. H04L 51/42
2022/0058663 A1 * 2/2022 Cui ...................... G06V 10/764
2023/0238145 A1 * 7/2023 Patel ...................... G16H 15/00 705/2
2023/0245777 A1 * 8/2023 Foschini ................ G16H 50/70 705/2
2025/0201360 A1 * 6/2025 Fernandes ............. G16H 10/60

OTHER PUBLICATIONS

Li, J., Yan, X.S., Chaudhary, D. et al. Imputation of missing values for electronic health record laboratory data. npj Digit. Med. 4, 147 (2021). (Year: 2021).*

Goldberger, et al., "PhysioBank, PhysioToolkit, and PhysioNet: Components of a New Research Resource for Complex Physiologic Signals," *Circulation* 101:e215-e220, Jun. 13, 2000. (6 pages).

(Continued)

*Primary Examiner* — Matthew L Hamilton
(74) *Attorney, Agent, or Firm* — Seed Intellectual Property Law Group LLP

(57) ABSTRACT

The present disclosure relates to predicting a data element in an electronic health record (EHR) for a subject using a trained machine learning model including an attention module. An example method includes obtaining a query for the prediction of the data element, obtaining a plurality of observations about the subject, processing the query and observations with the trained machine learning model having an attention module to generate a prediction of the subject characteristic, and providing the prediction of the data element as an output.

18 Claims, 12 Drawing Sheets

(56) References Cited

OTHER PUBLICATIONS

Heilbroner et al., "Life: A Deep Learning Framework for Laboratory Data Imputation in Electronic Health Records," Retrieved from https://www.medrxiv.org/content/10.1101/2023.10.31.23297843v1.full, posted Nov. 2, 2023. (50 pages).
International Search Report and Written Opinion, dated Mar. 12, 2024, for International Patent Application No. PCT/US2023/030239. (24 pages).
Ni et al., "MBGAN: An improved generative adversarial network with multi-head self-attention and bidirectional RNN for time series imputation," *Engineering Applications of Artificial Intelligence* 115, published online Aug. 1, 2022. (12 pages).
Oh et al., "STING: Self-attention based Time-series Imputation Networks using GAN," Cornell University Library, published online Sep. 22, 2022. (10 pages).
Van Buuren et al., "mice: Multivariate Imputation by Chained Equations in R," *Journal of Statistical Software* 45(3):1-67, Dec. 2011. (67 pages).
Angelopoulos et al., "A Gentle Introduction to Conformal Prediction and Distribution-Free Uncertainty Quantification," arXiv Preprint at http://arxiv.org/abs/2107.07511, Dec. 2022. (51 pages).
Ayilara et al., "Impact of Missing Data on Bias and Precision When Estimating Change in Patient-Reported Outcomes from a Clinical Registry," *Health and Quality of Life Outcomes* 17(106): 1-9, Jun. 2019.
Bodenreider et al., "Recent Developments in Clinical Terminologies—SNOMED CT, LOINC, and RxNorm," *IMIA Yearbook of Medical Informatics* 27(1): 129-139, Aug. 2018.
Cao et al., "BRITS: Bidirectional Recurrent Imputation for Time Series," *32nd Conference on Neural Information Processing Systems*, Montreal, Canada, Dec. 3-8, 2018, pp. 1-11.
Che et al., "Recurrent Neural Networks for Multivariate Time Series with Missing Values," *Scientific Reports* 8(6085): 1-12, Apr. 2018.
De Freitas et al., "Phe2vec: Automated Disease Phenotyping Based on Unsupervised Embeddings from Electronic Health Records," *Patterns 2*, 100337, Cell Press Open Access, Patterns Descriptor, Sep. 2021. (10 pages).
Dean et al., "Large Scale Distributed Deep Networks," NIPS'12: *Proceedings of the 25th International Conference on Neural Information Processing Systems—vol. 1*, Lake Tahoe, Nevada, Dec. 3-6, 2012, pp. 1-9.
Devlin et al., "BERT: Pre-Training of Deep Bidirectional Transformers for Language Understanding," ar Xiv Preprint at https://doi.org/10.48550/arXiv.1810.04805, May 2019. (16 pages).
Falconer et al., "Systematic Review of Predictive Risk Models for Adverse Drug Events in Hospitalized Patients," *British Journal of Clinical Pharmacology* 84: 846-864, Jan. 3, 2018.
Guo et al., "Characterizing the Limitations of Using Diagnosis Codes in the Context of Machine Learning for Healthcare," *medRxiv—Health Informatics*, http://medrxiv.org/lookup/doi/10.1101/2023.03.14.23287202, Mar. 2023. (26 pages).
Heilbroner et al., "Deep Learning in Medicine," *Clinical Journal of the American Society of Nephrology* 18(3): 397-399, Mar. 2023.
Horton et al., "Much Ado About Nothing: A Comparison of Missing Data Methods and Software to Fit Incomplete Data Regression Models," *NIH Public Access Author Manuscript, Am Stat*. 61(1), Available in PMC Mar. 2007. (24 pages).
Jensen et al., "Mining Electronic Health Records: Towards Better Research Applications and Clinical Care," *Nature Reviews Genetics 13, Transnational Genetics*: 395-405, Jun. 2012.
Johnson et al., "Data Descriptor: MIMIC-III, a Freely Accessible Critical Care Database," *Nature.com, Scientific Data* 3(160035): 1-9, May 2016.
Johnson et al., "MIMIC-III Clinical Database (v1.4)," *PhysioNet*, doi:10.13026/C2XW26, Sep. 2016. (6 pages).
Krishnan et al., "Self-Supervised Learning in Medicine and Healthcare," *Nature Biomedical Engineering* 6, Aug. 2022. (7 pages).
Landi et al., "Deep Representation Learning of Electronic Health Records to Unlock Patient Stratification at Scale," *Nature Partner Journals, Scripps Translational Institute, Digital Medicine* 3(96): 1-11, Jul. 2020.
LeCun et al., "Deep Learning," *Nature, Review*, vol. 521, May 2015. (10 pages).
Li et al., "Generic Medical Concept Embedding and Time Decay for Diverse Patient Outcome Prediction Tasks," *iScience, CellPress Open Access* 25(9): 104880, Sep. 16, 2022. (15 pages).
Li et al., "Imputation of Missing Values for Electronic Health Record Laboratory Data," *Nature Partner Journals, Digital Medicine* 4(147):1-14, Oct. 2021.
Luo et al., "3D-MICE: Integration of Cross-Sectional and Longitudinal Imputation for Multi-Analyte Longitudinal Clinical Data," *Journal of the American Medical Informatics Association* 25(6): 645-653, Jun. 2018.
Luo, Yuan, "Evaluating the State of the Art in Missing Data Imputation for Clinical Data," *Briefings in Bioinformatics* 23(bbab489): 1-9, Jan. 2022.
Ma et al., "Identifiable Generative Models for Missing Not at Random Data Imputation," *35th Conference on Neural Information Processing Systems (NeurIPS 2021), Online Conference*, Canada, Dec. 6-14, 2021, pp. 1-14.
McCord et al., "Using Electronic Health Records for Clinical Trials: Where do we Stand and Where Can we Go?," *Canadian Medical Association Journal* 191(5): E128-E133, Feb. 2019.
Miotto et al., "Deep Learning for Healthcare: Review, Opportunities and Challenges," *Briefings in Bioinformatics* 19(6): 1236-1246, Nov. 2018.
Pang et al., "CEHR-BERT: Incorporating Temporal Information from Structured EHR Data to Improve Prediction Tasks," *Proceedings of Machine Learning Research* 158:239-260, Dec. 2021.
Rasmy et al., "Med-BERT: Pretrained Contextualized Embeddings on Large-Scale Structured Electronic Health Records for Disease Prediction," *Nature Partner Journals, Digital Medicine* 4(86): 1-13, May 2021.
Schadow et al., "The Unified Code for Units of Measure," UCUM / UCUM Specification, Version: 2.1, pp. 1-84, https://ucum.org/trac, access date Nov. 29, 2021.
Scikit-Learn, 1.3.2 Documentation, "6.3. Preprocessing Data," pp. 1-16, https://scikit-learn.org/stable/modules/preprocessing.html, download date Nov. 13, 2023.
Shao et al., "Hybrid Value-Aware Transformer Architecture for Joint Learning from Longitudinal and Non-Longitudinal Clinical Data," medRxiv preprint at https://www.medrxiv.org/content/10.1101/2023.03.09.23287046v1, Mar. 2023. (10 pages).
Shickel et al., Deep Ehr: A Survey of Recent Advances in Deep Learning Techniques for Electronic Health Record (EHR) Analysis, *IEEE Journal of Biomedical and Health Informatics* 22(5): 1-45, Sep. 2018.
Shulman, David, "Optimization Methods in Deep Learning: A Comprehensive Overview," arXiv Preprint at https://doi.org/10.48550/arXiv.2302.09566, Feb. 2023. (5 pages).
Sun et al., "A Review of Deep Learning Methods for Irregularly Sampled Medical Time Series Data," ArXiv201012493, Cs Stat, pp. 1-20, Preprint at http://arxiv.org/abs/2010.12493, Oct. 2020.
Tomasev et al., "Developing Continuous Risk Models for Adverse Event Prediction in Electronic Health Records using Deep Learning," *Nature Protocols* 16, May 2021. (57 pages).
Van Buuren et al., "Mice: Multivariate Imputation by Chained Equations in R," Journal of Statistical Software 45(3): 1-67, Dec. 2011.
Van Ginkel et al., "Rebutting Existing Misconceptions About Multiple Imputation as a Method for Handling Missing Data," *Journal of Personality Assessmeny* 102(3), 2019. (13 pages).
Vaswani et al., "Attention Is All You Need," *31st Conference on Neural Information Processing Systems* (*NIPS* 2017), Long Beach, California, Dec. 4-9, 2017, pp. 1-15.
Xiao et al., "Opportunities and Challenges in Developing Deep Learning Models Using Electronic Health Records Data: a Systematic Review," *Journal of the American Medical Informatics Association* 25(10): 1419-1428, Jun. 2018.

(56) References Cited

OTHER PUBLICATIONS

Xu et al., "A Multi-Directional Approach for Missing Value Estimation in Multivariate Time Series Clinical Data," *Journal of Healthcare Informatics Research* 4(4): 365-382, Jun. 2020.

Yasrebi-de Kom et al., "Electronic Health Record-Based Prediction Models for in-Hospital Adverse Drug Event Diagnosis or Prognosis: a Systematic Review," *Journal of the American Medical Informatics Association* 30(5): 978-988, Feb. 2023.

Yoon et al., "Estimating Missing Data in Temporal Data Streams Using Multi-Directional Recurrent Neural Networks," *IEEE Transactions on Biomedical Engineering* 66: 1-15, Nov. 2017.

Yoon et al., "Multi-Directional Recurrent Neural Networks: A Novel Method for Estimating Missing Data," *ICML 2017 Time Series Workshop*, Sydney, Australia, Aug. 10-11, 2017. (5 pages).

* cited by examiner

SYSTEMS, METHODS, AND ARTICLES FOR IMPUTING DIRECTED TEMPORAL MEASUREMENTS

BACKGROUND

Technical Field

This disclosure relates generally to imputing directed temporal measurements, and more particularly, to using artificial intelligence (AI) models to impute directed temporal measurements.

Description of the Related Art

Patient lab tests are typically only ordered and documented to inform clinical decision making. Lab tests are often only reimbursed if there is a reasonable chance that the result could change the patient's management strategy. This means lab tests are most often ordered when they are likely to yield highly relevant information. Despite the clinical relevance of lab test results, there are many difficulties in systematically using lab test data. There are thousands of different lab test types. Typically, lab tests are grouped variously depending on the use case. Each lab test result can be notated in different units, and there is no reliable and automated way to standardize between these units.

BRIEF SUMMARY

A system of one or more computers can be configured to perform particular operations or actions by virtue of having software, firmware, hardware, or a combination of them installed on the system that in operation cause the system to perform the actions. One or more computer programs can be configured to perform particular operations or actions by virtue of including instructions that, when executed by one or more processors, cause the system to perform the actions. One aspect includes a method for imputing a value associated with a subject within an electronic health record (EHR) system. The method includes receiving a request to impute the value associated with the subject at a temporal instance. The method also includes retrieving a subset of data associated with the subject from the EHR system, the subset of data may include a plurality of stored values associated with one or more temporal instances. The method also includes providing the temporal instance indicated in the request and the subset of data to a trained artificial intelligence engine. The trained artificial intelligence engine is configured to perform actions, including determining relationships between the stored values, the relationships being determined by calculating a set of scores for multiple subsets of features of the stored values that represent interdependencies between the stored values; adjusting the calculated scores based on a temporal proximity of the one or more temporal instances of the stored values relative to the temporal instance of the value being imputed to generate time-adjusted scores; generating an imputed value by creating a weighted combination of the stored values, where the weights are determined based on the time-adjusted scores for the multiple subsets of features of the stored values; and providing the imputed value in response to the request. Other embodiments of this aspect include corresponding computer systems, apparatus, and computer programs recorded on one or more computer storage devices, each configured to perform the actions of the methods.

Implementations may include one or more of the following features. The subset of data may be associated with the subject. In at least some implementations, the request includes a unit of measure. Adjusting the calculated scores based on the temporal proximity of the one or more temporal instances of the stored values relative to the temporal instance of the value being imputed may include applying a time decay function to the calculated scores that is dependent on differences between the temporal instance of the value being imputed and the one or more temporal instances of the stored values in the EHR. The time decay function may include an exponential time decay function or a linear time decay function, for example. Adjusting the calculated scores based on the temporal proximity of the one or more temporal instances of the stored values relative to the temporal instance of the value being imputed may include applying more weight to stored values that are relatively nearer in time to the temporal instance of the value being imputed.

Determining the relationships between the stored values in the EHR may include use of a multi-head attention module. Generating an imputed value may include applying a weight matrix to the time-adjusted scores to combine them into a single representation, and processing the single representation using a classifier to generate the imputed value. Applying a weight matrix to the time-adjusted scores may include using a Hadamard product module. Processing the single representation to generate the imputed value may include using a multilayer perceptron module. In at least some implementations, the method may include predicting an occurrence of an adverse event based on the imputed value, or assessing a predicted eligibility for a clinical trial based on the imputed value, or predicting a gap in care based on the imputed value. The imputed value may include a lab test value, or a characteristic evaluated by a clinical assessment. The stored values may include at least one prior lab test result, or at least one prior clinical assessment result. The temporal instance of the value being imputed may include a date. Implementations of the described techniques may include hardware, a method or process, or computer software on a computer-accessible medium.

One general aspect includes a computing system for imputing a value associated with a subject within a structured electronic health record (EHR) system. The computing system also includes one or more processors. The system also includes one or more non-transitory computer-readable media collectively storing instructions that, when collectively executed by the one or more processors, cause the one or more processors to perform actions. The actions may include receiving a request to impute the value associated with the subject at a temporal instance; retrieving a subset of data associated with the subject from the EHR system, the subset of data may include a plurality of stored values associated with one or more temporal instances; and providing the temporal instance indicated in the request and the subset of data to a trained artificial intelligence engine. The trained artificial intelligence engine may be configured to perform actions, including determining relationships between the stored values, the relationships being determined by calculating a set of scores for multiple subsets of features of the stored values that represent interdependencies between the stored values; adjusting the calculated scores based on a temporal proximity of the one or more temporal instances of the stored values relative to the temporal instance of the value being imputed to generate time-adjusted scores; generating an imputed value by creating a weighted combination of the stored values, where the weights are determined based on the time-adjusted scores for the multiple subsets of features of the stored values; and providing the imputed value in response to the request. Other embodiments of this aspect include corresponding computer systems, apparatus, and computer programs recorded on one or more computer storage devices, each configured to perform the actions of the methods.

Embodiments described herein can improve the operation of the computing system for generating a prediction of a data element. Lab test values can be efficiently imputed from a wide variety of prior lab test results. By learning relationships between different types of lab test results, embodiments described herein eliminate the need to spend compute cycles attempting to standardize heterogeneous lab test results across large electronic health record datasets. By imputing lab test values as opposed to running more lab tests, laboratory computing resources are conserved, improving the efficiency of laboratory computers. Further, patient health outcomes are improved by imputing lab values, as important but missing data critical to healthcare decision making can be reconstructed. This saves lab, healthcare, and computing resources. Data elements can be more readily assessed, leading to more accurate diagnosis and treatment, less follow-up diagnostic testing and subsequent data processing, and reduced electronic health record database access requests by doctors attempting to diagnose or treat patients with incomplete data.

BRIEF DESCRIPTION OF THE DRAWINGS

The implementations of this disclosure are illustrated by way of example and not limitation in the figures of the accompanying drawings, in which like references indicate similar elements and in which.

Figure 1:
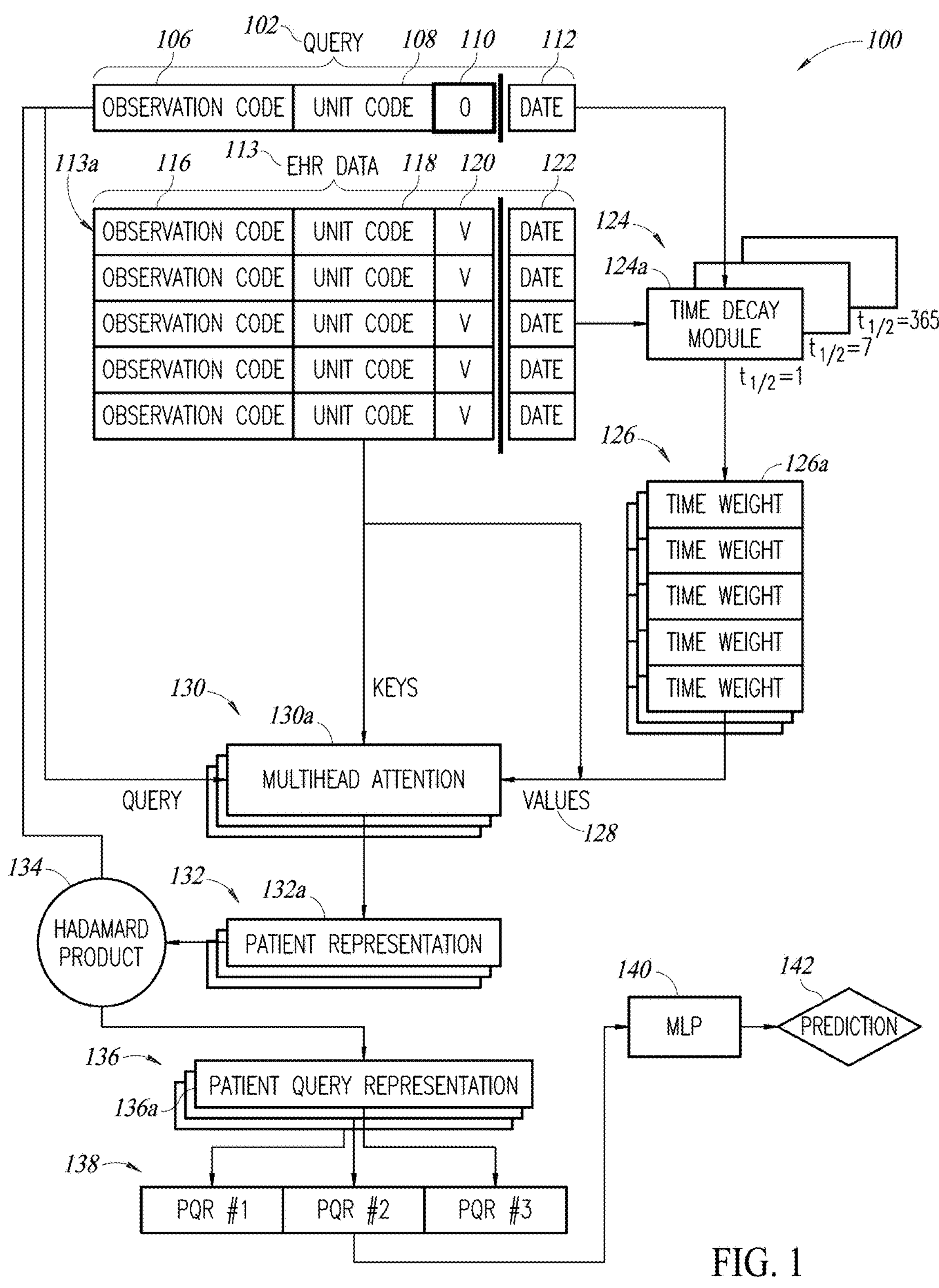
FIG. 1 is a block diagram illustrating an example machine learning architecture for lab value imputation in accordance with at least some implementations of the techniques described herein.

Other features of the present embodiments will be apparent from the accompanying drawings and from the detailed description that follows.

DETAILED DESCRIPTION

The following description, along with the accompanying drawings, sets forth certain specific details to provide a thorough understanding of various disclosed embodiments. However, one skilled in the relevant art will recognize that the disclosed embodiments may be practiced in various combinations, without one or more of these specific details, or with other methods, components, devices, materials, etc. In other instances, well-known structures or components that are associated with the environment of the present disclosure, including but not limited to the communication systems and networks and the environment, have not been shown or described in order to avoid unnecessarily obscuring descriptions of the embodiments. Additionally, the various embodiments may be methods, systems, media, or devices. Accordingly, the various embodiments may combine software and hardware aspects.

Throughout the specification, claims, and drawings, the following terms take the meaning explicitly associated herein, unless the context clearly dictates otherwise. The term "herein" refers to the specification, claims, and drawings associated with the current application. The phrases "in one embodiment," "in another embodiment," "in various embodiments," "in some embodiments," "in other embodiments," and other variations thereof refer to one or more features, structures, functions, limitations, or characteristics of the present disclosure, and are not limited to the same or different embodiments unless the context clearly dictates otherwise. As used herein, the term "or" is an inclusive "or" operator, and is equivalent to the phrases "A or B, or both" or "A or B or C, or any combination thereof," and lists with additional elements are similarly treated. The term "based on" is not exclusive and allows for being based on additional features, functions, aspects, or limitations not described, unless the context clearly dictates otherwise. In addition, throughout the specification, the meaning of "a," "an," and "the" include singular and plural references.

References to the term "set" (e.g., "a set of items"), as used herein, unless otherwise noted or contradicted by context, is to be construed as a nonempty collection comprising one or more members or instances.

References to the term "subset" (e.g., "a subset of the set of items"), as used herein, unless otherwise noted or contradicted by context, is to be construed as a nonempty collection comprising one or more members or instances of a set or plurality of members or instances.

Moreover, the term "subset," as used herein, refers to a proper subset, which is a collection of one or more members or instances that are collectively smaller in number than the set or plurality of which the subset is drawn. For instance, a subset of a set of ten items will have less than ten items and at least one item.

Continuous values in a system may at any time be measured and placed into a record. The record may be reviewed to observe performance of a subject. In many domains, gathering, recording, and storing continuous values relevant to the performance of a subject is expensive. For example, in the domain of medical care, some measurements of data elements like red blood cell count are invasive and may require the patient to visit a care facility and give a blood sample. Imputing measurements like these from known continuous values in a patient's existing record can therefore save considerable expense. While patients are a subject targeted by embodiments of the present disclosure, the systems, methods, and articles described herein may be applied to a variety of other systems such as mechanical systems, weather systems, and the like.

When the subject is a patient, the continuous values may include measurements such as blood pressure, heart rate, rate of blood flow through an artery, lung capacity, oxygen saturation, and other measurable qualities of the patient. Other continuous values observable in a patient include values assessed by interview or otherwise. For example, the continuous values may include the results of assessments for mental health disorders, personality traits, intelligence, motor functioning, and the like. The results of these assessments may be, for instance, a number of answers indicative of a mental health condition or a percentile performance of a motor functioning test.

Continuous values observed in a patient may further include measurements that are taken invasively, such as a diagnostic test to identify levels of specific substances in samples from the patient including measurements such as A1C, red blood cell count, those found in metabolic or blood panel, and all other traditional diagnostic results.

Many diagnostic predictors based on machine learning and electronic health records (EHRs) would benefit from more complete data. Embodiments of the present disclosure help provide more complete data by imputing continuous values from other correlated continuous values and therefore improve EHR-based algorithms.

An adverse event is an event that is an undesirable outcome. In a medical context, adverse events are events in which care resulted in an undesirable outcome not caused by underlying disease that, for example, prolongs a patient's stay, causes patient harm, requires life-saving intervention, or contributes to death. Machine learning models based on EHRs are often built to predict adverse events to drive care decisions. Missing or incomplete data negatively affects the performances of these models. Imputing continuous values to be used in ML models that predict adverse events improves the quality of these models, and consequently the quality of patient care.

Clinical trial eligibility is often tied to lab test results. Often, lab test results are not available for a subject for a variety of reasons, including (1) the subject did not take the test; (2) the test results were not made available by the hospital; (3) the test was taken in a different hospital; (4) the test is not temporally significant (e.g., the test was taken too long ago to be relevant to the present day or falls outside of a date range criteria to be included); and (5) the last test results were unsatisfactory, despite being temporally relevant and the algorithm identifies an expected shift in their results that bring them into eligibility for the clinical trial. Some of these subjects with missing lab test results would otherwise be eligible for a certain clinical trial but are rendered ineligible due to the missing lab test results. Imputing continuous values for lab tests at various points in time increases the availability of clinical trials to subjects by increasing the number of subjects for which qualifying lab test results are available.

A "gap in care" is defined as a discrepancy between recommended best practices for a subject's care and the care that a subject receives. For example, a gap in care occurs when a person is overdue for a recommended screening like an annual mammogram, colonoscopy, or well visit based on their age or other risk factors. Another gap in care occurs when a person does not follow a recommendation for taking a prescription medication to manage a specific condition like diabetes. A person does not share with their provider how a newly prescribed medication from another doctor might interfere with their medication; and so on. "Care Gap Algorithms" analyze EHRs to identify missing values and alert clinicians. Laboratory test results are information used in Care Gap Algorithms to identify, for example, missing therapies. Inferring missing values by embodiments of the present disclosure increases the quality of laboratory test results and will therefore benefit the performance of Care Gap Algorithms.

High or low levels of certain substances in a body can be a sign of cancer. Laboratory tests of blood, urine, and other body fluids that measure these substances can help doctors make a diagnosis. But some labs that may be helpful in diagnosing cancer are often not ordered and are not part of standard care. Imputing the continuous value results for these missing laboratory tests from the other data points could assist subjects with or at risk of developing cancer, increasing the chances of positive outcomes.

Because lab tests are only ordered when they are likely to be clinically relevant, the lab test results are typically missing not at random (MNAR). Additionally, lab test results vary over time and tend to be sparse, making imputation of missing values difficult but necessary. Finally, representing uncertainty in lab test value imputation is difficult because there is often not enough data to reliably predict a continuous lab probability distribution. These factors make imputing and using lab test values difficult. What is needed is a way to impute lab test values from existing subject data.

FIG. 1 is a block diagram illustrating an example machine learning architecture 100 for lab value imputation in accordance with at least some implementations of the techniques described herein. The exemplary machine learning architecture 100 begins at query 102 having query event code 106 (also referred to as an observation code), query unit code 108, query value 110, and query date 112. Query 102 serves as input for time decay module 124, multi-head attention module 130, and combiner module 134. The query 102 may be generated in any number of ways. For example, a large set of lab tests of interests may be specified and their value may be inferred for each patient of interest encounter (or time point) of interest. In the context of an interactive tool, a user may specify the query, e.g., via one or more dropdown menus or other interface elements. In at least some implementations, free-text queries with a natural language processing (NLP)/named entity recognition (NER) model on top may be used to extract the entities of interest (e.g., lab test name, unit of measure, and date). Large language models (LLMs) may also be used to structure free-text. Further, the values predicted may be searched with a clinical trial search or LENS search, for example.

Electronic health record (EHR) data 113 includes at least one example observation 113*a* (five observations shown in FIG. 1). Example observation 113*a* includes event code 116, unit code 118, value 120, and observation date 122. EHR data 113 is input to multi-head attention module 130, which determines the relevance of each observation in EHR data 113 including observation 113*a* with respect to predicting query value 110 in query 102 and time weights 126. Multi-head attention module 130 takes query 102, EHR data 113, and time-weighted values 128 as inputs. Time-weighted values 128 are the elementwise product of time weights 126 and EHR data 113. Multi-head attention module 130 outputs patient representations 132, which is a vector embedding of patient EHR data 113 relevant to query 102. Combiner module 134 takes query 102 and patient representations 132 as input and computes the Hadamard product of the two vectors, resulting in patient query representations 136, which are concatenated into concatenated patient query representation 138. Concatenated patient query representation 138 is input for classifier module 140, which computes prediction 142 as output. Prediction 142 is a continuous variable representing the prediction by machine learning model 100 of query value 110 in query 102.

According to some embodiments, query 102 includes a plurality of observation queries corresponding to a plurality of query values 110 to be imputed. Query 102 may be a concatenation of query event code 106, query unit code 108, query value 110, and query date 112. In some embodiments, query 102 is an embedding besides concatenation based on query event code 106, query unit code 108, query value 110, and query date 112. Query 102 may not have values for each element described above. For example, an International Classification of Disease (ICD) code observation consists of only an event code, with no corresponding unit code or value. According to some embodiments, null values in query 102 are replaced with zeros. According to some embodiments, at least one of query event code 106, query unit code 108, query value 110, and query date 112 are embedded into a vector space using learned embeddings. The architecture may generate the embeddings during training, similar to principal component analysis (PCA) or an autoencoder. They are trained by minimizing the loss function during self-supervised training (e.g., with masking). The information loss is minimized by this technique. During inference, e.g., when imputing a lab value, the code is mapped to the embedding, which may be stored in the model. There may also be a dictionary that maps codes to embeddings/weights in the model.

As noted above, the queries may be generated by iterating across several codes or patients and time points, or a user may manually provide the queries in various ways. In addition, the system may use codes available in structured EHRs by running queries in the corresponding tables and retrieving the codes, which may be normalized to specific ontologies if needed. For EHRs containing unstructured text, the system may extract codes using NLP or other techniques.

Query event code 106 indicates a type of lab test associated with an observation. Query event code 106 may be an International Classification of Disease (ICD) code, a Logical Observation Identifier Names and Codes (LOINC) code, a Current Procedural Terminology (CPT) code, or any other known lab test coding system. For example, ICD code C34 represents lung cancer, while LOINC code 2857-1 represents prostate specific antigen ("prostate specific Ag"). According to some embodiments, query event code 106 is mapped to an integer. According to some embodiments, query event code 106 is embedded into a vector space using learned embeddings. Query event code 106 may be embedded, for instance, into a 1024-dimensional space. Query event code 106 is, according to various embodiments, embedded into a 512-dimensional space, a 2048-dimensional space, or a space of any other suitable dimension. Preferably, the dimensionality of the space is a power of two, i.e., 2, 4, 8, 16, 32, etc.

Query unit code 108 represents the unit of measurement of a queried lab test. According to some embodiments, a null valued query unit code 108 is replaced with zero. Query unit code 108 represents the unit of measurement of an observation. Query unit code 108 may be formatted according to SNOMED Clinical Terms or any other known unit code format. For example, a SNOMED Clinical Terms unit code of 258683005 connotes a weight unit of measurement in kilograms. According to some embodiments, query unit code 108 is given a value indicating no unit of measurement is available for the observation.

Query value 110 is according to some embodiments a continuous variable indicating a value of an observation to be predicted. Because query value 110 is the value to be predicted, machine learning architecture 100 typically does not have access to query value 110. Therefore, query value 110 is typically set to zero. Query value 110 may according to some embodiments include a query discrete value representing a discrete value to be predicted. Similarly, the query discrete value is often inaccessible as it is the value being predicted. According to some embodiments, the query discrete value is set to null. Query value 110 is according to some embodiments mapped to a uniform distribution between 0 and 1 using a quantile transform that maps a value to a percentile in a population of values.

Query date 112 indicates the date at which to predict query value 110. Query date 112 is in some embodiments a present date if a current lab test value of a patient is being predicted. In some embodiments, query date 112 is a date in the past or a date in the future. Query date 112 is according to some embodiments a string formatted in YYYYMMDD format, YYYY-MM-DD format, or any other date format. According to some embodiments, query date 112 is mapped to an integer representing the number of days from the earliest observation in the patient's EHR data 113.

Electronic health record (EHR) data 113 contains at least one observation associated with the patient query 102. According to some embodiments, example observation 113*a* includes event code 116, unit code 118, value 120, and observation date 122. In some embodiments, example observation 113*a* is a learned embedding based on event code 116, unit code 118, value 120, and observation date 122. Example observation 113*a* may not have values for each element described above. For example, an International Classification of Disease (ICD) code observation consists of only an event code, with no corresponding unit code or value. According to some embodiments, null values in EHR data 113 are replaced with zeros.

Event code 116, according to some embodiments, describes the type of observation being made in example observation 113*a*. Event code 116 may be an International Classification of Disease (ICD) code, a Logical Observation Identifier Names and Codes (LOINC) code, a Current Procedural Terminology (CPT) code, or any other known lab test coding system. According to some embodiments, event code 116 is embedded into a vector space using learned embeddings. Event code 116 may be embedded, for instance, into a 1024-dimensional space.

Unit code 118 represents the unit of measurement of an observation. Unit code 118 may be formatted according to SNOMED Clinical Terms or any other known unit code format. According to some embodiments, unit code 118 is given a value indicating no unit of measurement is available for the observation.

Value 120 is a variable indicating a value of an observation. According to some embodiments, value 120 is mapped to a uniform distribution on [0, 1] using a quantile transform, and then 0.5 is subtracted from the results of the quantile transform to zero-center the result. The quantile transform maps values to [0, 1] using their corresponding quantile value. For example, a patient height value of 74 inches is mapped to 0.97, because a height of 74 inches corresponds to the $97^{th}$ percentile in height over a population of height values.

Observation date 122 indicates the date on which an observation in EHR data 113 was made. Observation date 122 is according to some embodiments a string formatted in YYYYMMDD format, YYYY-MM-DD format, or any other date format. According to some embodiments, observation date 122 is an integer equal to the number of days that have elapsed between the date of the earliest observation in EHR data 113 and observation date 122.

Time decay module 124 takes EHR data 113 and query 102 as input. Time decay module 124 assigns different weights to each observation in EHR data 113 based on how close its date is to query date 112. According to some embodiments, time decay module 124 weights EHR data observations by exponential decay based on their recency. For each observation, a weight is determined using the formula:

$$w = 2^{(D_q - D_o)/t_{1/2}}$$

Where w is the weight, $D_q$ is query date 112, $D_o$ is observation date 122, and $t_{1/2}$ is the half-life. The half-life can be modified to weigh the recency of EHR data 113 differently. For example, a half-life of 1 weighs the recency of EHR data 113 relatively higher in determining its relevance. A half-life of 365 weights the recency of EHR data 113 relatively lower in determining its relevance. A half-life approaching infinity would cause all EHR data 113 to be weighed equally regardless of when it was collected relative to query date 112. By contrast, a half-life approaching zero would render all observations but those collected on query date 112 irrelevant.

According to some embodiments, more than one half-life value is selected. For example, a first half-life is 1, a second half-life is 7, and a third half-life is 365, as depicted in FIG. 1. According to various embodiments, any number of half-life values may be selected. In some instances, the one or more half-life values may be determined based on weights that are learned in end-to-end training of the trained machine learning model. In the example illustrated in FIG. 1, time decay module 124 includes three time decay networks including example time decay network 124*a*. Each time decay network computes a set of time weights corresponding to the selected half-life value. For example, time weights set 126*a* corresponds to the half-life of 1 used in example time decay network 124*a*. Each set of time weights is then provided as input to a different multi-head attention network 130*a* in multi-head attention module 130, resulting in set of three corresponding patient representations in patient representations 132 including patient representation 132*a*, and later a set of three patient query representations 136 including patient query representation 136*a*. The resulting three patient representation queries 136 are then concatenated together into concatenated patient query representation 138. The operation of each multi-head attention network 130*a* in multi-head attention module 130 is described below.

Multi-head attention module 130 includes at least one multi-head attention network 130*a*. In at least some implementations, the multi-head attention module 130 may be similar to the modules described in Vaswani et al. "Attention is All You Need," Advances in Neural Information Processing Systems 40, Pages 5998-6008, which is incorporated by reference in its entirety. The multi-head attention network 130*a* includes at least one attention network, or "head," described below. In general, an "attention" mechanism lets the model learn what to focus on based on the input data. The "multi-head" part means that the model has multiple, independent attention mechanism heads that each produce their own output in parallel. These outputs may then be concatenated and linearly transformed to produce the final output. An advantage of having multiple heads is that each one can potentially learn to pay attention to different types of information (e.g., different types of relationships in the data). By combining the outputs from multiple heads, the model can potentially capture a wider range of relationships in the data compared to using a single attention head. Scaled dot-product attention or other types of attention mechanisms may be used.

In at least some implementations, an attention network takes a query, a key, and a value as input. According to some embodiments, the query is an e dimensional vector query 102, the key is an n×e dimensional tensor EHR data 113, and the value is an n×e dimensional tensor time-weighted values 128. The attention network applies a separate e×e tensor of weights trained by backpropagation to query 102, EHR data 113, and time-weighted values 128 by matrix multiplication. This results in an n×e dimensional query tensor (Q), an n×e dimensional EHR data tensor (K), and an n×e dimensional values tensor (V), respectively. Q, K, and V are then used to compute an attention score tensor according to the following equation, where $d_k$ is the length of query 102:

$$\text{Attention}(Q, K, V) = \text{softmax}\left(\frac{QK^T}{\sqrt{d_k}}\right)V$$

Each of the one or more attention networks included in multi-head attention network 130*a* produces an attention score tensor as described above. These attention score tensors are then concatenated together to produce each e dimensional patient representation in patient representations 132, including patient representation 132*a*.

According to some embodiments, machine learning architecture 100 includes a plurality of multi-head attention modules connected in series. For example, patient representations 132 as produced by multi-head attention module 130 may serve as a query input for another multi-head attention module also taking EHR data 113 and time-weighted values 128 as inputs. The second multi-head attention module then outputs patient representations 132. In a similar way, any number of multi-head attention modules may be connected in series, with each multi-head attention module in the series taking the output of the previous module as a query input, along with EHR data 113 and time-weighted values 128 as inputs. The output of the last multi-head attention module in the series is patient representations 132.

Patient representations 132 includes at least one patient representation 132*a*, which is an e dimensional tensor representing a patient's EHR data 113 with respect to query 102 and time weights set 126*a*. In at least some implementations, only a portion of a patient's EHR data may be utilized. For example, all features that appear less than N (e.g., 5) times may be discarded. As another example, only data that is more likely to relate to a particular disease may be selected, using a co-occurrence analysis or similar process. As another example, only data that is capture within a certain time period may be used (e.g., within 1 year, within 5 years). An embodiment according to FIG. 1 includes three patient representations, each corresponding to a set of time weights in time weights 126. According to some embodiments, patient representations 132 are normalized before being input into combiner module 134. For example, patient representations 132 may be batch normalized as described in Ioffe et. al "Batch Normalization: Accelerating Deep Network Training by Reducing Internal Covariate Shift," which is incorporated by reference in its entirety. According to various embodiments, patient representations 132 may be batch normalized according to any known batch normalization technique, or any other known normalization technique including layer normalization, group normalization, instance normalization, and the like.

Combiner module 134 takes query 102 and patient representations 132 as input and generates patient query representations 136 as output. According to some embodiments, combiner module 134 computes the Hadamard product of query 102 and each patient representation in patient representations 132, resulting in patient query representations 136. Then, the patient query representations 136 are concatenated together, yielding concatenated patient query representation 138.

Classifier module 140 takes concatenated patient query representation 138 as input and outputs prediction 142. According to some embodiments, classifier module 140 includes a multilayer perceptron. According to some embodiments, classifier module 140 includes a sigmoid activation function such that its output prediction 142 is a scalar value between 0 and 1 corresponding to a prediction of a quantile value of query value 110. According to various embodiments, any known activation function may be used including a ReLU activation function, a linear activation function, a Tan h activation function, and the like. According to some embodiments, classifier module 140 outputs prediction 142 corresponding to discrete values. For instance, prediction 142 could correspond to a measure of certainty that query 102 belongs to the same patient EHR data 113 is taken from. In this way, discrete values such as the presence or absence of a queried disease, are predicted.

Figure 2A:
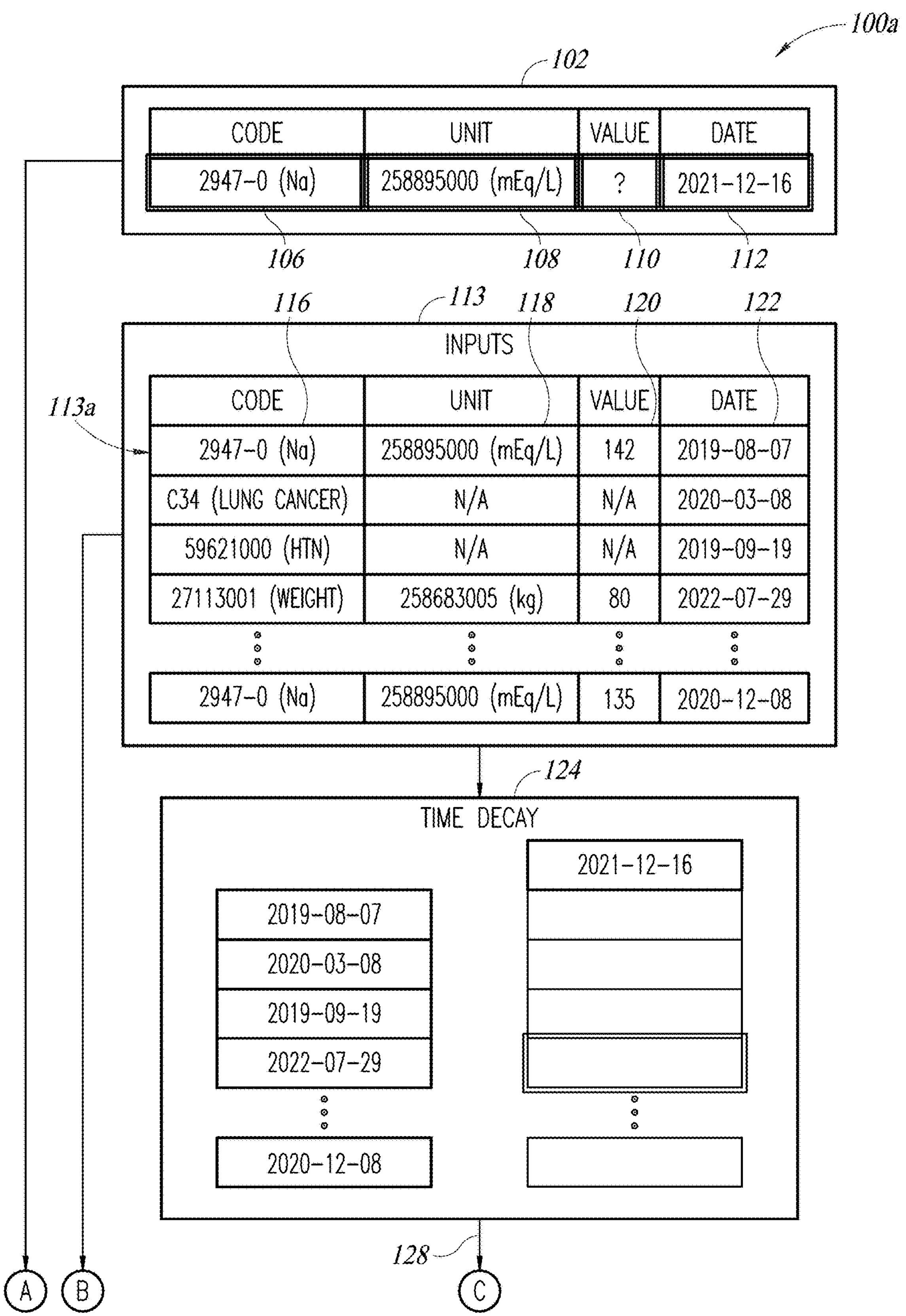
FIGS. 2A-2B are a block diagram illustrating an example machine learning architecture for lab value imputation with exemplifying values in accordance with at least some implementations of the techniques described herein.
Figure 2B:
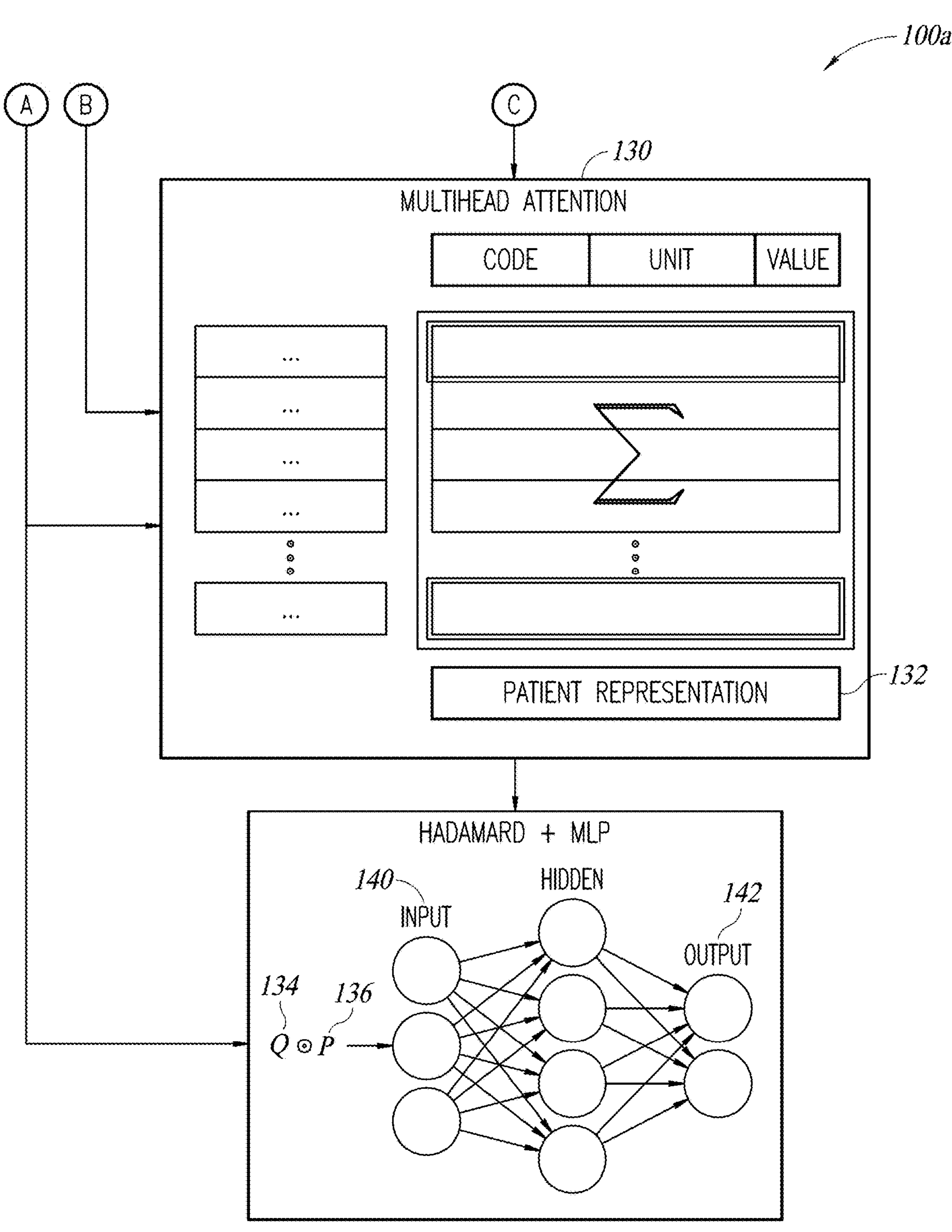

FIGS. 2A-2B are a block diagram illustrating an example machine learning architecture 100*a* for lab value imputation with exemplifying values in accordance with at least some implementations of the techniques described herein. The example machine learning architecture 100*a* may be similar or identical to the example machine learning architecture 100 described with respect to FIG. 1 above. Accordingly, a detailed discussion of the architecture 100*a* is not repeated herein in the interest of brevity. Machine learning architecture 100*a* includes query 102, EHR data 113, time decay module 124, multi-head attention module 130, patient representations 132, combiner module 134, and classifier module 140 (e.g., multilayer perceptron).

Query 102 includes query event code 106, query unit 108, query value 110, and query date 112. EHR data 113 includes at least one observation 113*a* with event code 116, unit 118, value 120, and observation date 122. Multi-head attention module 130 receives time-weighted values 128, query 102, and the EHR data 113 as inputs. Multi-head attention module 130 outputs patient representation 132 to combiner module 134, which computes the Hadamard product of patient representation 132 and query 112, resulting in patient query representations 136. Patient query representations 136 is then concatenated together and provided as input to classifier module 140. Classifier module 140 outputs a prediction 142 for query value 110.

Figure 3:
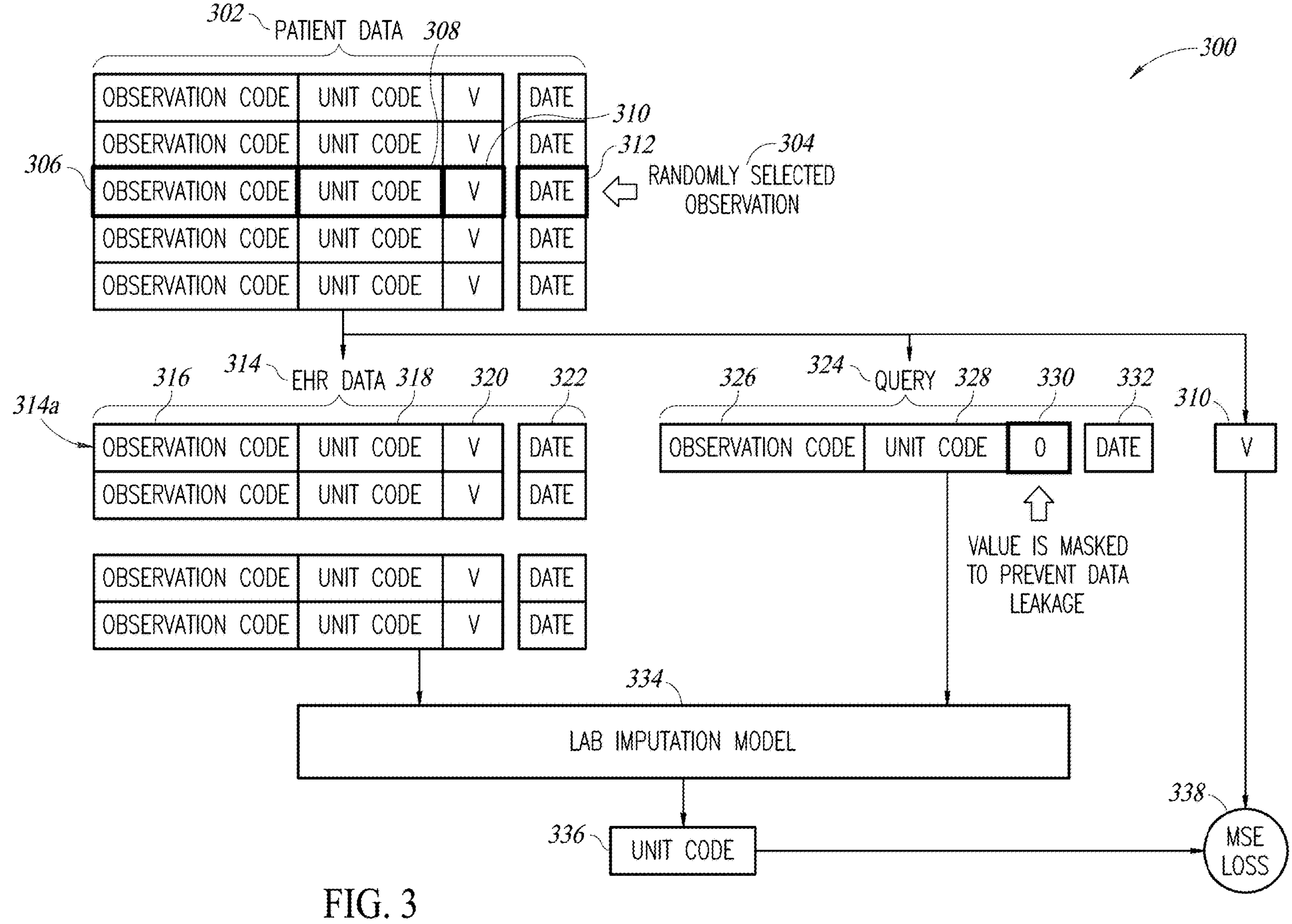
FIG. 3 is a block diagram illustrating a training process for an example machine learning architecture for imputation of a continuous lab value variable in accordance with at least some implementations of the techniques described herein.

FIG. 3 is a block diagram illustrating a training process 300 for an example machine learning architecture for imputation of a continuous lab value variable in accordance with at least some implementations of the techniques described herein. Training process 300 includes patient data 302, EHR data 314, query 324, and lab imputation model 334.

Patient data 302 includes a plurality of observations about a patient. Observation 304 is randomly selected from the plurality of observations. EHR data 314 is patient data 302 with observation 304 removed. EHR data 314 contains at least one example observation 314*a* having event code 316, unit code 318, value 320, and date 322. Query 324 is randomly selected observation 304 with its value 310 set to zero to prevent data leakage. Query value 330 is zero, query event code 326 is event code 306, query unit code 328 is unit code 308, and query date 332 is date 312. Lab imputation model 334 takes EHR data 314 and query 324 as input, and outputs prediction 336, which is compared to value 310 using loss function 338. Loss function 338 may be mean squared error (MSE) loss or any other suitable loss function. Model weights in lab imputation model 334 are then updated by backpropagation based on the loss computed at loss function 338.

Figure 4:
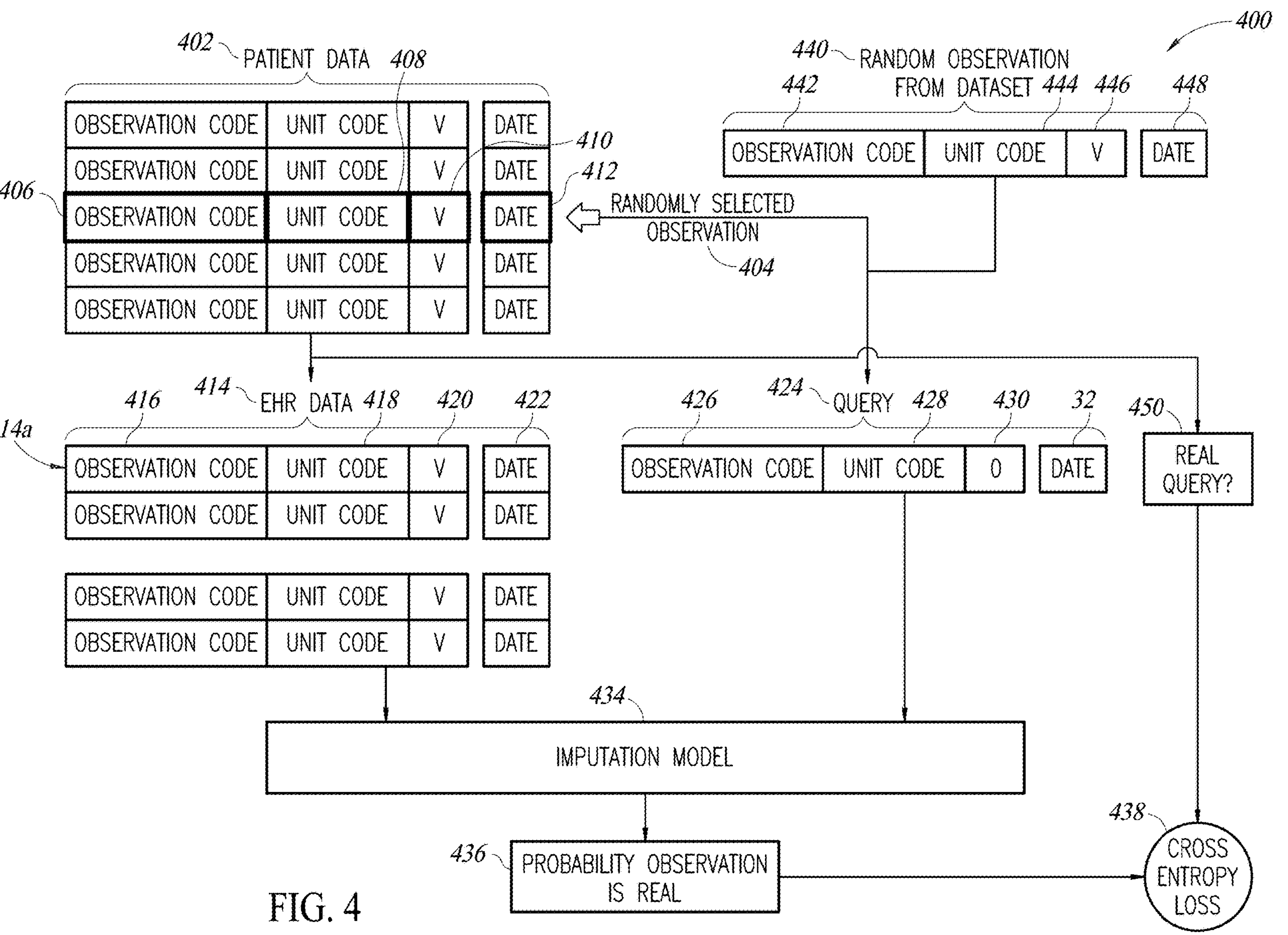
FIG. 4 is a block diagram illustrating a training process for an example machine learning architecture for imputation of a discrete lab value variable in accordance with at least some implementations of the techniques described herein.
Figure 5A:
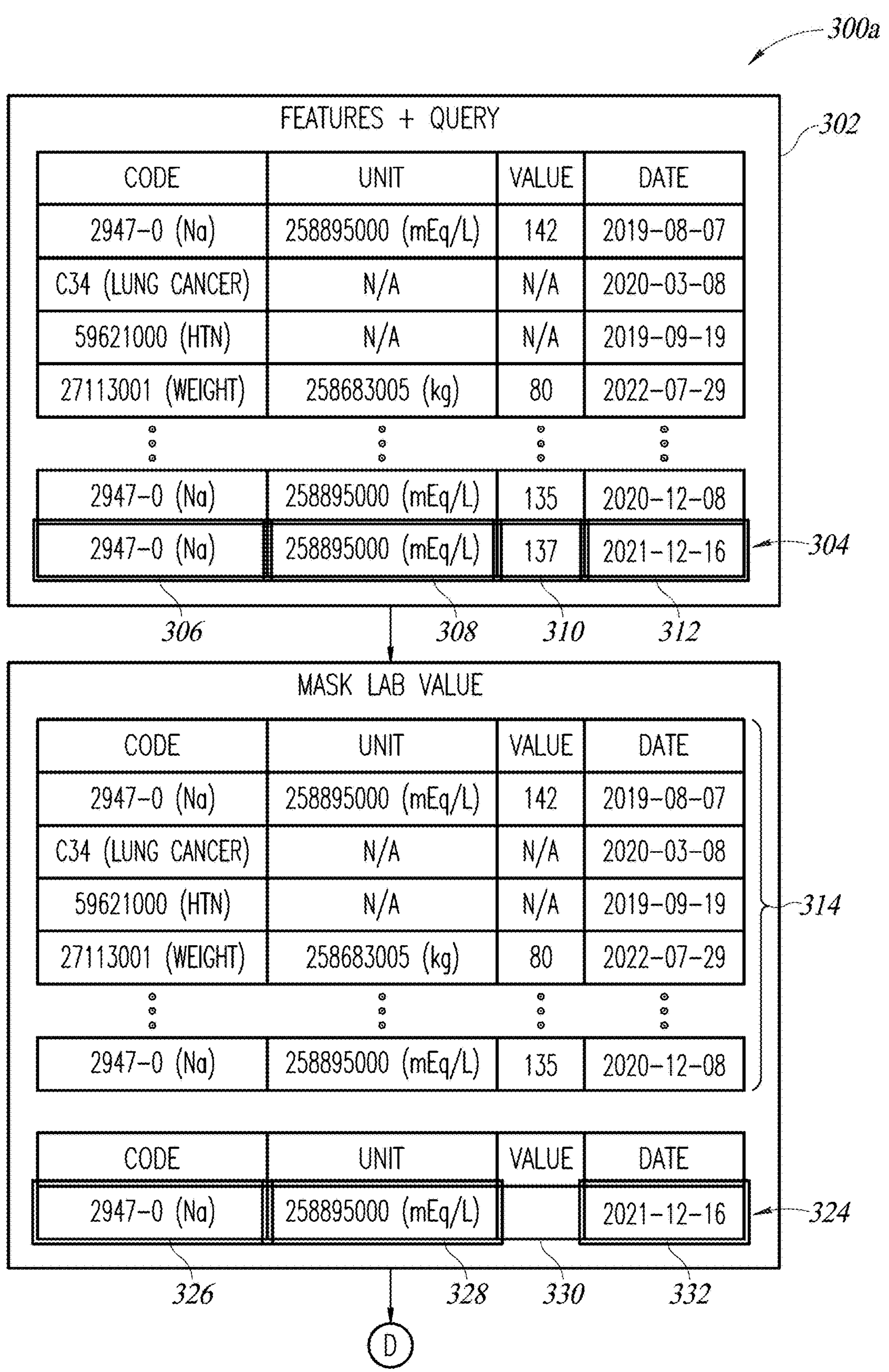
FIGS. 5A-5B are a block diagram illustrating a training process for an example machine learning architecture for imputation of a continuous lab value variable with exemplifying values in accordance with at least some implementations of the techniques described herein.
Figure 5B:
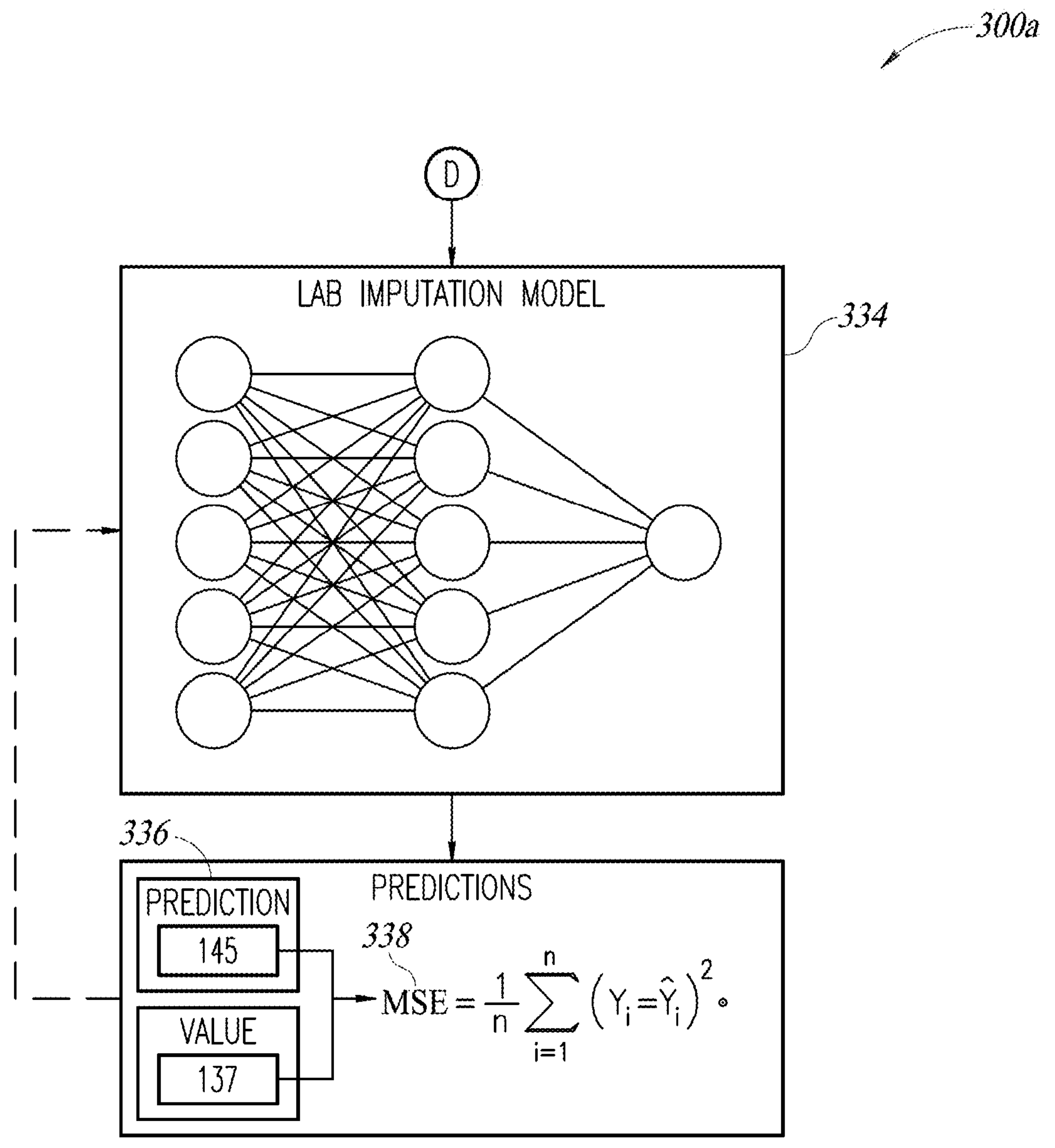

FIG. 4 is a block diagram illustrating a training process 400 for an example machine learning architecture for imputation of a discrete lab value variable in accordance with at least some implementations of the techniques described herein. Training process 400 includes patient data 402, which includes a plurality of observations about a patient from which observation 404 is selected at random. Random observation 440 is taken from a different, random patient's data. Query 424 is either observation 404 or random observation 440, with its value for 410 or 446, respectively, set to 0. Query 424's value 430 is zero and its query event code 426, query unit code 428, and query date 432 are taken from the analogous fields of either observation 404 or random observation 440. According to some embodiments, observation 404 is selected 50% of the time as the basis for query 424, and random observation 440 is selected 50% of the time as the basis for query 424. According to various embodiments, the relative frequencies with which observation 404 and random observation 440 are selected as the basis for query 424 vary. EHR data 414 is patient data 402 with observation 404 removed. EHR data 414 includes at least one example observation 414*a*, having event code 416, unit code 418, value 420, and date 422. Imputation model 434 takes EHR data 414 and query 424 as input, and outputs prediction 436, which represents whether query 424 is taken from patient data 402. Binary value 450 is one if query 424 was based on observation 404, and zero if query 424 was based on a random observation 440. Binary value 450 and prediction 436 are then compared using loss function 438. Model weights are then updated based on the loss computed at loss function 438. FIGS. 5A-5B are a block diagram illustrating training process 300*a* for an example machine learning architecture for imputation of a continuous lab value variable with exemplifying values in accordance with at least some implementations of the techniques described herein. FIG. 5 proceeds similarly to FIG. 3.

Patient data 302 includes a plurality of observations about a patient. Observation 304 is randomly selected from the plurality of observations, and contains event code 306, unit code 308, value 310, and date 312. EHR data 314 is patient data 302 with randomly selected observation 304 removed. Query 324 is observation 304 with its value 310 set to zero to prevent data leakage. Query event code 326 is event code 306, query unit code 328 is unit code 308, query value 330 is zero, and query date 332 is date 312. Lab imputation model 334 takes EHR data 314 and query 324 as input, and outputs prediction 336, which is compared to value 310 using loss function 338. Model weights are then updated based on the loss computed at loss function 338.

Figure 6:
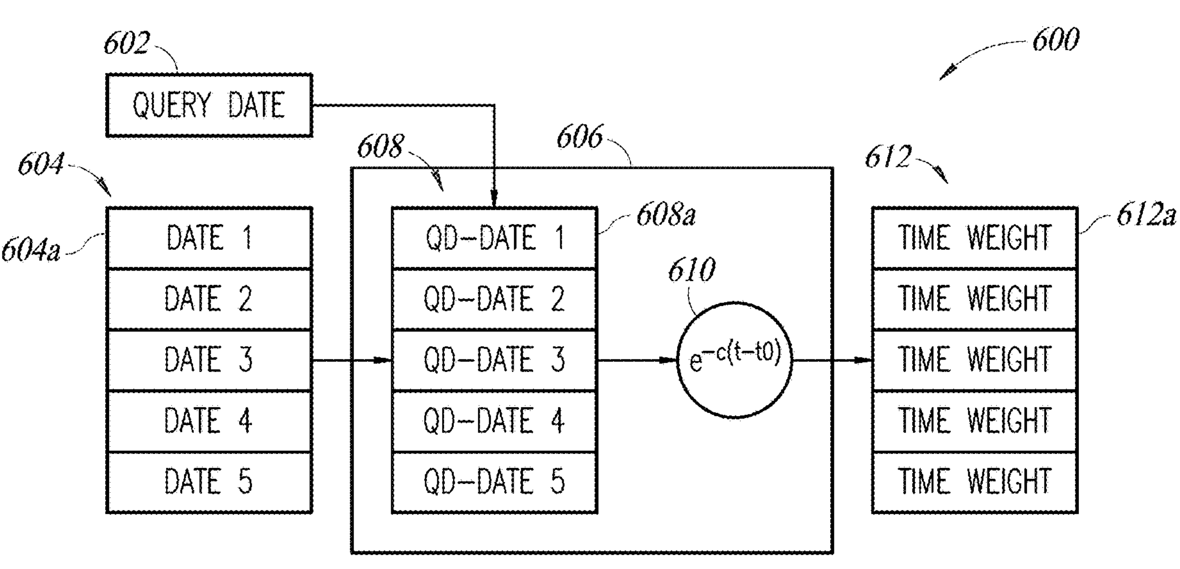
FIG. 6 is a block diagram illustrating a time decay module of a machine learning architecture for imputation of a lab value variable in accordance with at least some implementations of the techniques described herein.

FIG. 6 is a block diagram illustrating a time decay module 600 of a machine learning architecture for imputation of a lab value variable in accordance with at least some implementations of the techniques described herein. The time decay module 600 may be similar or identical to the time decay modules discussed elsewhere herein. Query date 602 is a date for which a query is being made. Dates 604 including date 604*a* are dates corresponding to observations about the patient for which the query is being made. Shifted dates 608 including shifted date 608*a* are calculated by taking the difference between query date 602 and each date in dates 604. Time decay function 610 is applied to shifted dates 608, producing time weights 612, including time weight 612*a*.

According to some implementations, time decay function 610 is an exponential time decay function as described with respect to FIG. 1. Time decay function 610 may also, according to some implementations, be a linear decay function, a stepwise decay function, a logistic decay function, or any other suitable decay function. Parameters of time decay function 610 may be modified to produce different time decay characteristics. In some instances, the parameters of time decay function 610 are based on weights that are learned in end-to-end training of the trained machine learning model.

Figure 7:
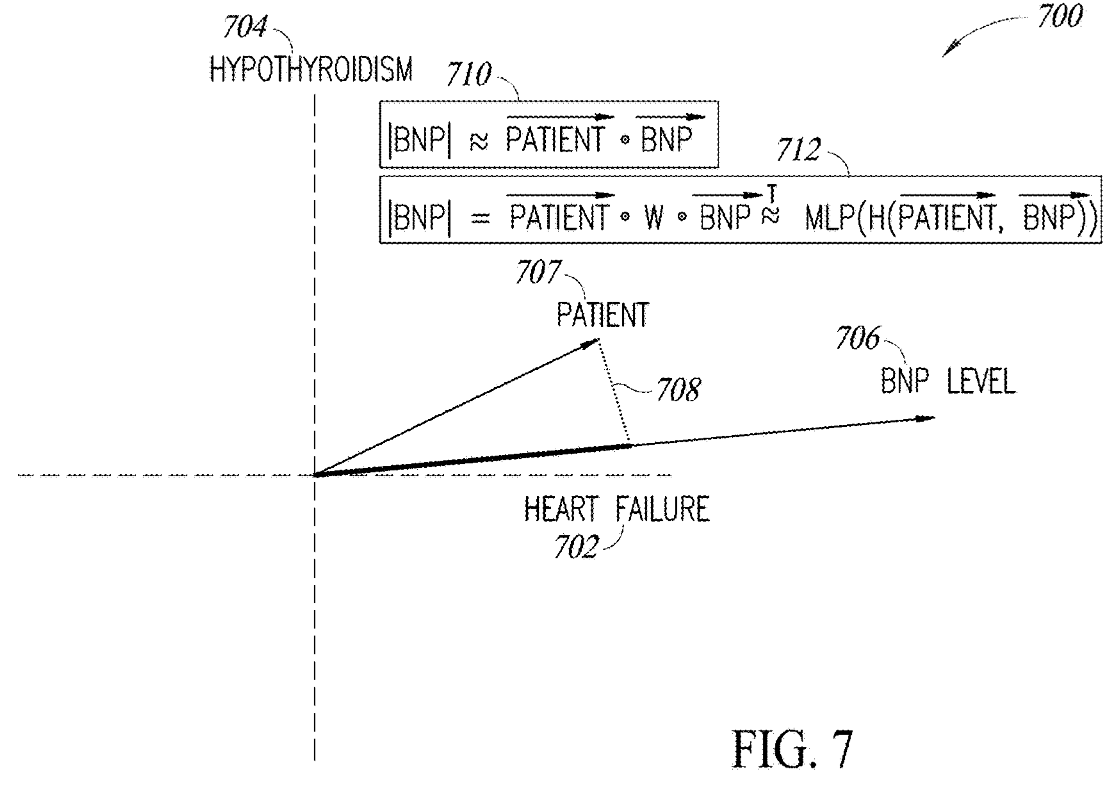
FIG. 7 is a diagram illustrating the effect of applying a multilayer perceptron to a Hadamard product of a patient representation and a query vector in accordance with at least some implementations of the techniques described herein.

FIG. 7 is a diagram illustrating the effect of applying a multilayer perceptron to a Hadamard product of a patient representation and a query vector in accordance with at least some implementations of the techniques described herein. Diagram 700 includes heart failure axis 702 and hypothyroidism axis 704. Patient vector 707 is an embedding of a patient's hypothyroidism and heart failure. Query vector 706 represents a patient lab value to be predicted, in this case BNP level. The magnitude of the patient's BNP level 708 can be obtained by taking the dot product 710 of patient vector 707 and query vector 706. Hadamard product and multilayer perceptron operation 712 also determines the magnitude of the patient's BNP level using patient vector 707 and query vector 706. The product measures the distance between the embeddings (if the lab value is very related to the patient status) and the multilayer perception allows for prediction of the value based on the association. For example, if a patient has a diagnosis of Type 2 Diabetes (T2D) on a certain date, it is expected that the value of A1C would be high. The algorithm models this so those values can be inferred even when they are not available. Although a Hadamard product and multilayer perceptron are described herein, a dot-product or any techniques that multiply and aggregate vectors into a single value may be used.

Figure 8:
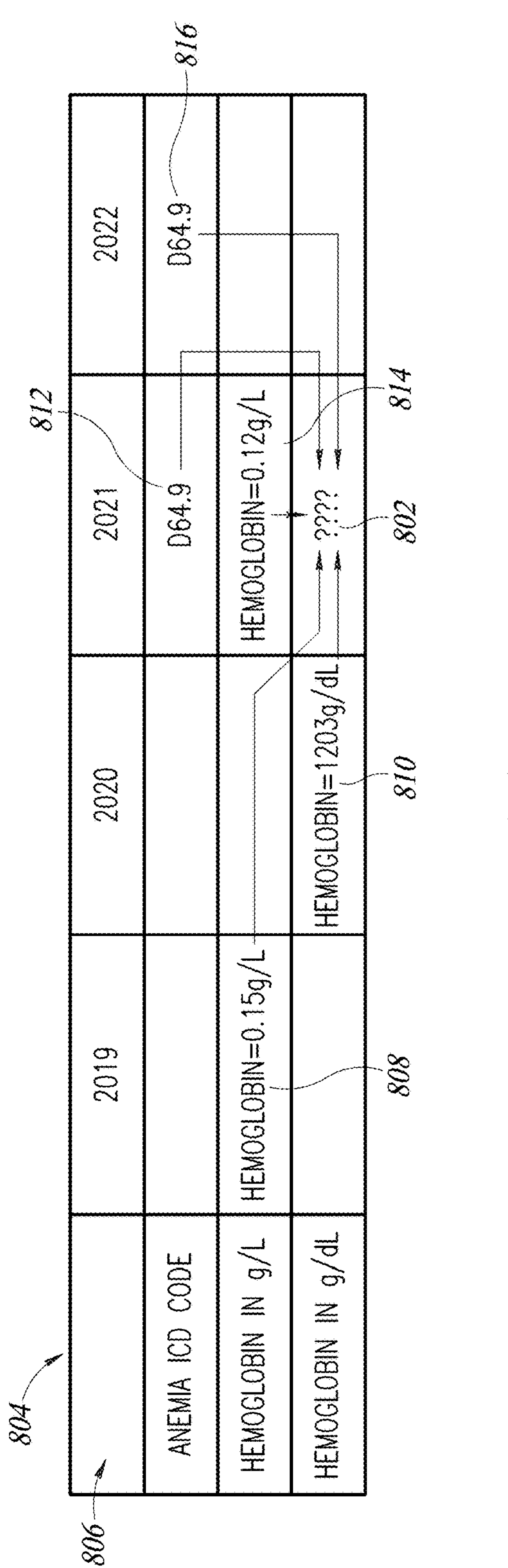
FIG. 8 is a table illustrating the use of prior lab test results for imputation of a lab value variable in accordance with at least some implementations of the techniques described herein.

FIG. 8 is a table 800 illustrating the use of prior lab test results for imputation of a lab value variable in accordance with at least some implementations of the techniques described herein. In the depicted case, table 800 contains lab test results organized by year 806 and test type 804. The value of queried variable 802 is unknown. But closely related values, previous values, and future values can be used to predict queried variable 802. For example, lab result 808 has the same test type as queried value 802 but has a different year and unit. Lab result 810 has the same test type as queried variable 802 but is for a different year 806. Lab result 812 is for a different test type than queried variable 802 but has the same year 806. Lab result 814 has the same year and test type as queried variable 802, but has different units. Lab result 816 is from a date subsequent to the query date of queried variable 802. Implementations of the techniques described herein are capable of using at least each of the depicted categories variable values to predict queried variable 802.

Figure 9:
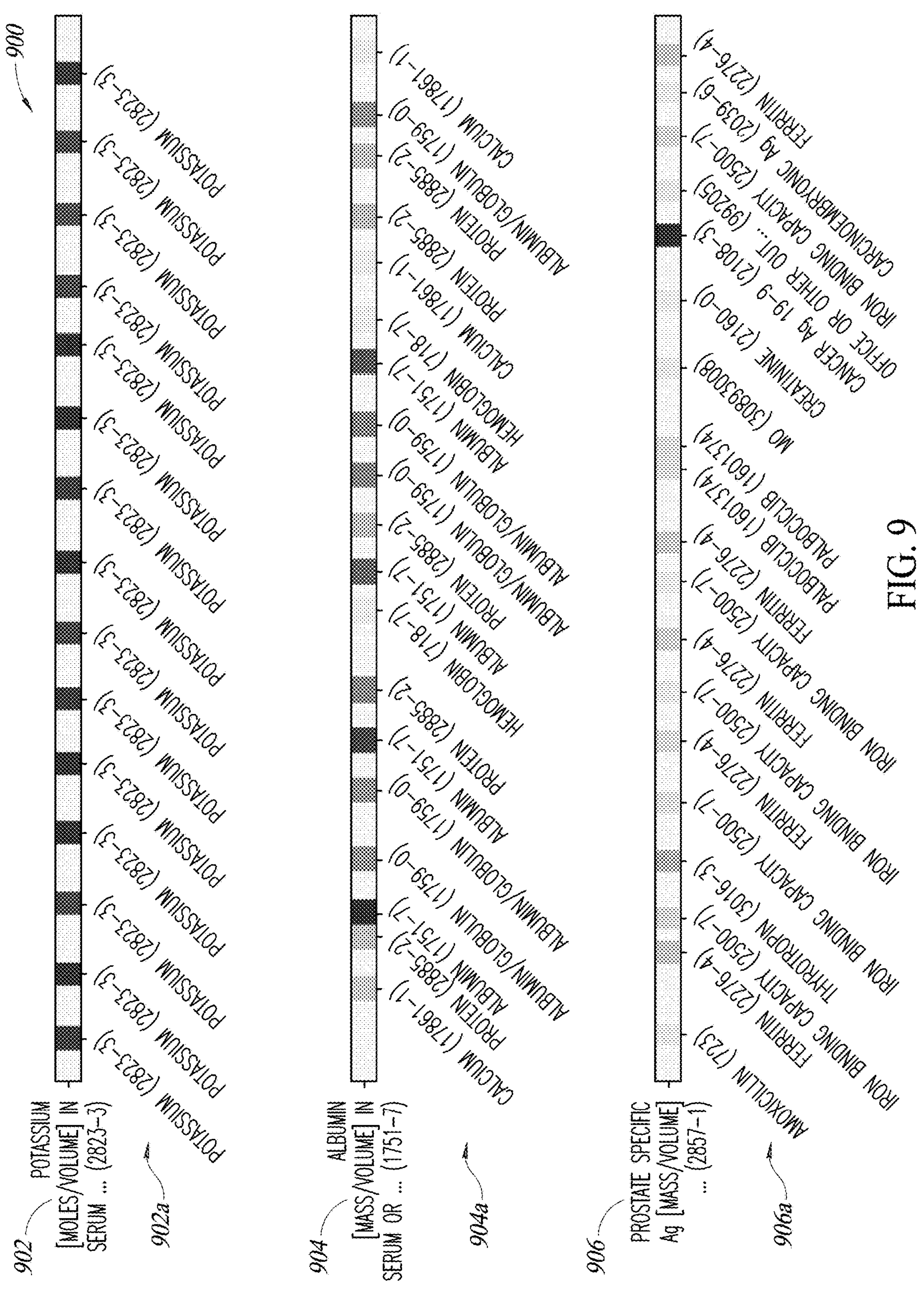
FIG. 9 is a visualization of the significance of various prior lab test results in imputation of lab test values as determined by a multi-head attention module in accordance with at least some implementations of the techniques described herein.

FIG. 9 is a visualization 900 of the significance of various lab test results in imputation of a lab test value as determined by a multi-head attention module in accordance with at least some implementations of the techniques described herein. In each heatmap 902, 904, and 906, the shade of each cell indicates the predictive relevance of each corresponding lab test result for the value in question. Lightly shaded cells indicate the corresponding lab test result has less predictive relevance for the value in question, and heavily shaded cells indicate the corresponding lab test result has more predictive relevance for the value in question. Potassium heatmap 902 illustrates the relevance of various potassium lab values including value 902*a* in predicting potassium [Moles/volume] in Serum. Albumin heatmap 904 illustrates the relevance of various lab test values including value 904*a* in predicting Albumin [Mass/volume] (1751-7) in serum. As expected, Albumin (1751-7) values are heavily shaded and thus are highly predictive of Albumin (1751-7). But other test values such as Protein (2885-2) are shaded and thus also have predictive relevance, allowing prediction of Albumin (1751-7) with test values besides Albumin (1751-7) itself. Prostate specific Ag heatmap 906 illustrates the relevance of various lab test values including value 906*a* in predicting prostate specific Ag (2857-1). Here, there is no lab test for prostate specific Ag (2857-1), but the multi-head attention module has determined that cancer Ag 19-9 (24108-3) is highly relevant in predicting prostate specific Ag (2857-1). Therefore, prostate specific Ag can still be predicted absent a lab test value for prostate specific Ag.

Figure 10:
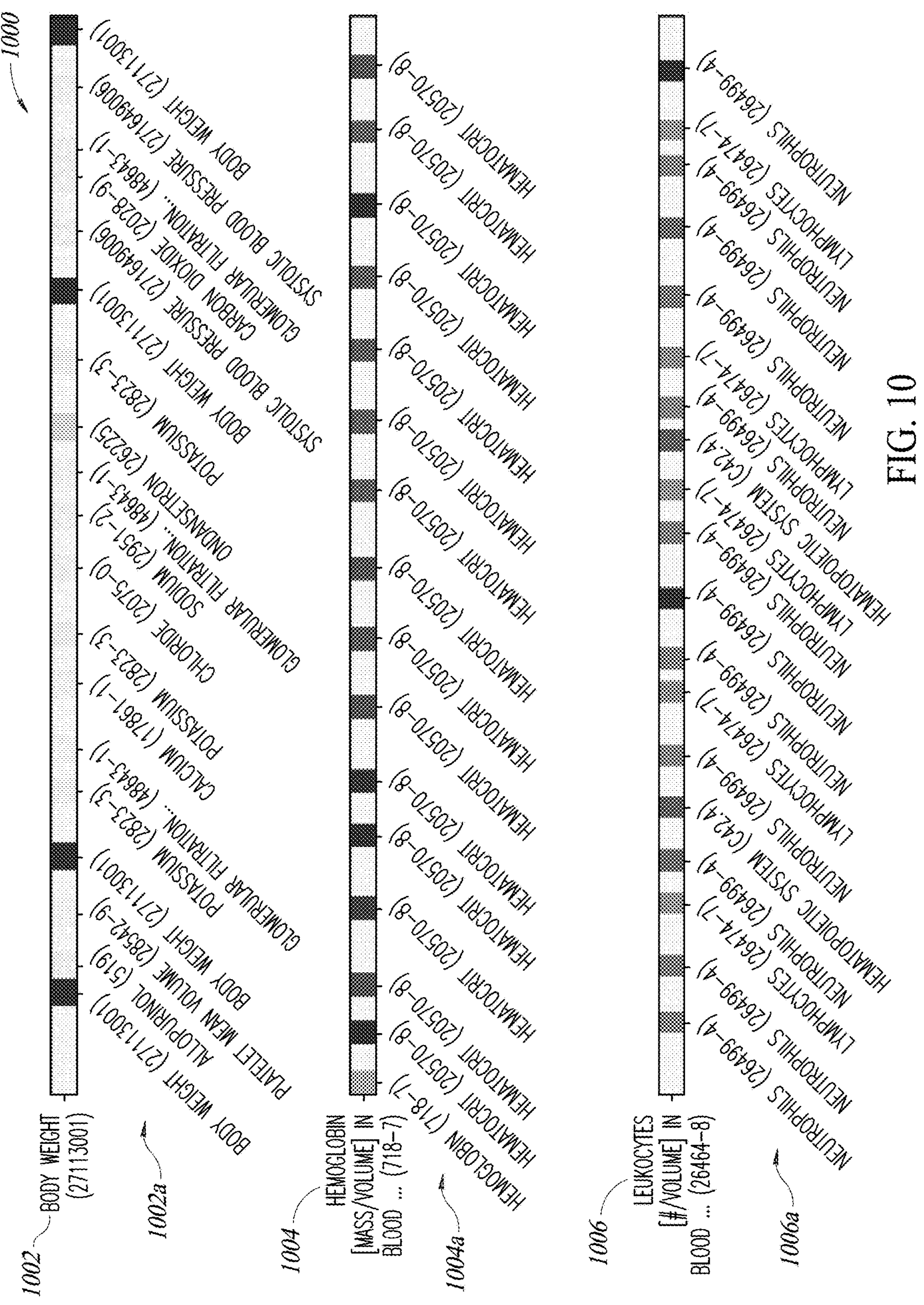
FIG. 10 is a visualization of the significance of various prior lab test results in imputation of lab test values as determined by a multi-head attention module in accordance with at least some implementations of the techniques described herein.

FIG. 10 is a visualization 1000 of the significance of various prior lab test results in imputation of a lab test value as determined by a multi-head attention module in accordance with at least some implementations of the techniques described herein. Similar to FIG. 9, in each heatmap 1002, 1004, and 1006, lightly shaded cells indicate the corresponding lab test result has less predictive relevance for the value in question and heavily shaded cells indicate the corresponding lab test result has more predictive relevance. Body weight heatmap 1002 including value 1002*a* shows that body weight lab values have high predictive relevance for body weight, while other lab test values have low predictive relevance. Hemoglobin in blood heatmap 1004 including value 1004*a* shows that hematocrit lab values have high predictive relevance for hemoglobin in blood. Leukocytes in blood heatmap 1006 including value 1006*a* shows that neutrophils lab test values have high predictive relevance for leukocytes in blood.

Figure 11:
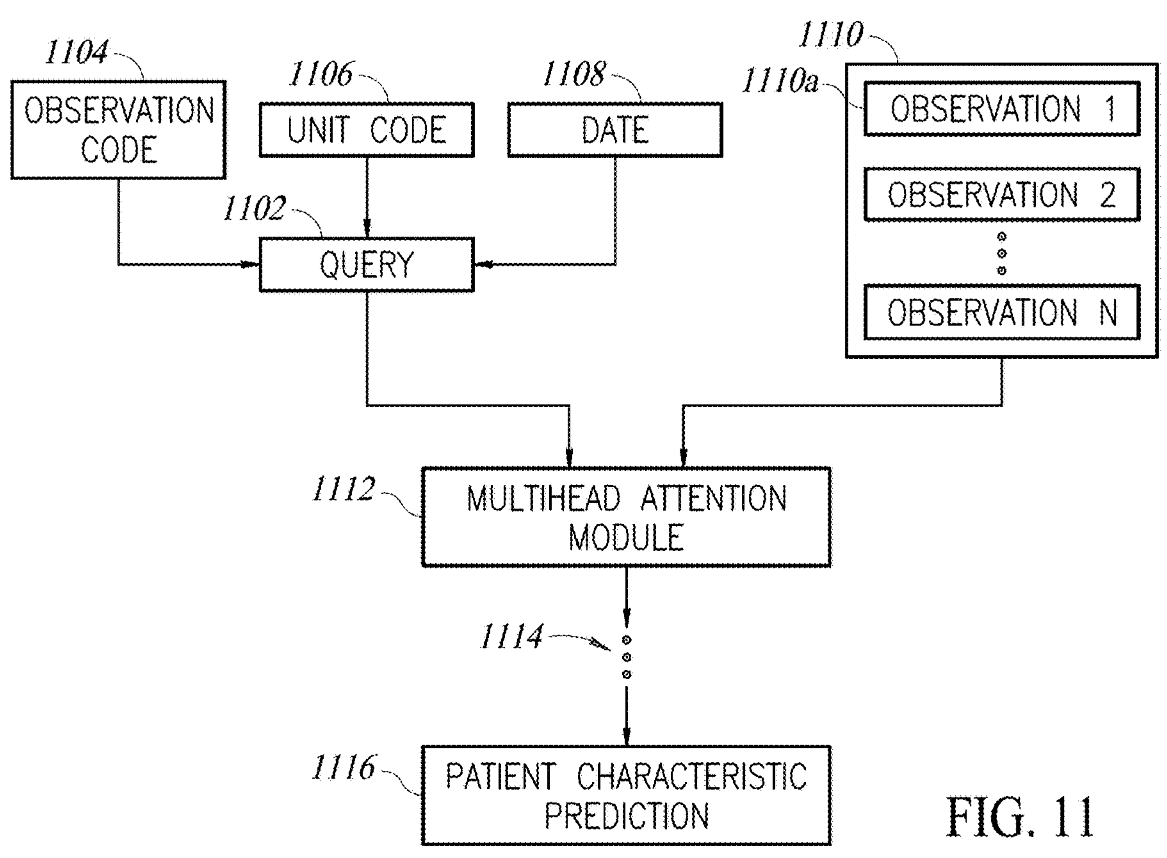
FIG. 11 is a flow diagram illustrating selected steps in imputation of a lab test value in accordance with at least some implementations of the techniques described herein.

FIG. 11 is a flow diagram 1100 illustrating selected steps in imputation of a lab test value in accordance with at least some implementations of the techniques described herein. FIG. 11 proceeds similarly to FIG. 1. Query 1102 includes event code 1104, unit code 1106, and date 1108. Observations 1110 includes at least one observation 1110*a* about a patient. Multi-head attention module 1112 takes query 1102 and observations 1110 as input and outputs patient representation 1114. Patient representation 1114 is then used to predict a subject characteristic 1116.

Figure 12:
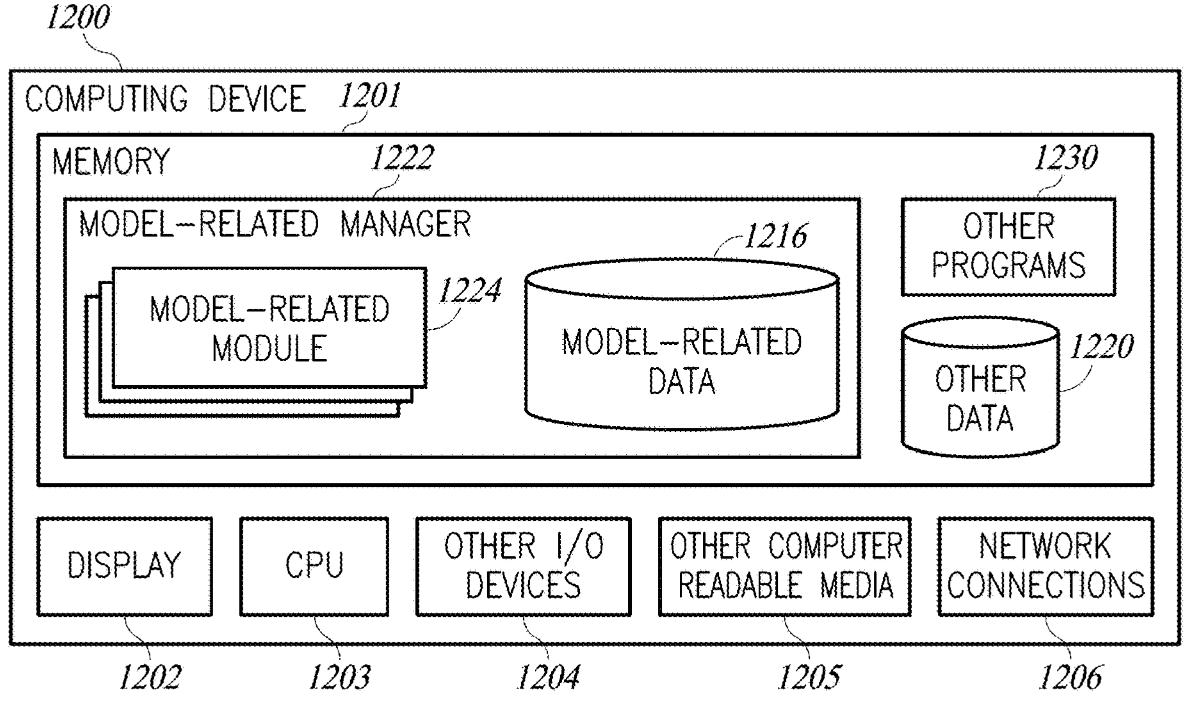
FIG. 12 is a diagram illustrating selected elements of a machine learning model for imputation of a lab test value in accordance with at least some implementations of the techniques described herein.

FIG. 12 is a block diagram illustrating selected elements of an example computing device 1200 utilized in accordance with at least some embodiments of the techniques described herein.

In some embodiments, one or more general purpose or special purpose computing systems or devices may be used to implement the computing device 1200. In addition, in some embodiments, the computing device 1200 may comprise one or more distinct computing systems or devices, and may span distributed locations. Furthermore, each block shown in FIG. 12 may represent one or more such blocks as appropriate to a specific embodiment or may be combined with other blocks. Also, the model-related manager 1222 may be implemented in software, hardware, firmware, or in some combination to achieve the capabilities described herein.

As shown, the computing device 1200 comprises a non-transitory computer memory ("memory") 1201, a display 1202 (including, but not limited to a light emitting diode (LED) panel, cathode ray tube (CRT) display, liquid crystal display (LCD), touch screen display, projector, etc.), one or more Central Processing Units ("CPU") or other processors 1203, Input/Output ("I/O") devices 1204 (e.g., keyboard, mouse, RF or infrared receiver, universal serial bus (USB) ports, High-Definition Multimedia Interface (HDMI) ports, other communication ports, and the like), other computer-readable media 1205, and network connections 1206. The model-related manager 1222 is shown residing in memory 1201. In other embodiments, some portion of the contents and some, or all, of the components of the model-related manager 1222 may be stored on or transmitted over the other computer-readable media 1205. The components of the computing device 1200 and model-related manager 1222 can execute on one or more CPUs 1203 and implement applicable functions described herein. In some embodiments, the model-related manager 1222 may operate as, be part of, or work in conjunction or cooperation with other software applications stored in memory 1201 or on various other computing devices. In some embodiments, the model-related manager 1222 also facilitates communication with peripheral devices via the I/O devices 1204, or with another device or system via the network connections 1206.

The one or more model-related modules 1224 is configured to perform actions related, directly or indirectly, to AI or other computational model(s). In some embodiments, the model-related module(s) 1224 stores, retrieves, or otherwise accesses at least some model-related data on some portion of the model-related data storage 1216 or other data storage internal or external to the computing device 1200.

Other code or programs 1230 (e.g., further data processing modules, a program guide manager module, a Web server, and the like), and potentially other data repositories, such as data repository 1220 for storing other data, may also reside in the memory 1201, and can execute on one or more CPUs 1203. Of note, one or more of the components in FIG. 12 may or may not be present in any specific implementation. For example, some embodiments may not provide other computer readable media 1205 or a display 1202.

In some embodiments, the computing device 1200 and model-related manager 1222 include API(s) that provides programmatic access to add, remove, or change one or more functions of the computing device 1200. In some embodiments, components/modules of the computing device 1200 and model-related manager 1222 are implemented using standard programming techniques. For example, the model-related manager 1222 may be implemented as an executable running on the CPU 1203, along with one or more static or dynamic libraries. In other embodiments, the computing device 1200 and model-related manager 1222 may be implemented as instructions processed by a virtual machine that executes as one of the other programs 1230. In general, a range of programming languages known in the art may be employed for implementing such example embodiments, including representative implementations of various programming language paradigms, including but not limited to, object-oriented (e.g., Java, C++, C#, Visual Basic.NET, Smalltalk, and the like), functional (e.g., ML, Lisp, Scheme, and the like), procedural (e.g., C, Pascal, Ada, Modula, and the like), scripting (e.g., Perl, Ruby, Python, JavaScript, VBScript, and the like), or declarative (e.g., SQL, Prolog, and the like).

In a software or firmware implementation, instructions stored in a memory configure, when executed, one or more processors of the computing device 1200 to perform the functions of the model-related manager 1222. In some embodiments, instructions cause the CPU 1203 or some other processor, such as an I/O controller/processor, to perform at least some functions described herein.

The embodiments described above may also use well-known or other synchronous or asynchronous client-server computing techniques. However, the various components may be implemented using more monolithic programming techniques as well, for example, as an executable running on a single CPU computer system, or alternatively decomposed using a variety of structuring techniques known in the art, including but not limited to, multiprogramming, multithreading, client-server, or peer-to-peer, running on one or more computer systems each having one or more CPUs or other processors. Some embodiments may execute concurrently and asynchronously, and communicate using message passing techniques. Equivalent synchronous embodiments are also supported by a model-related manager 1222 implementation. Also, other functions could be implemented or performed by each component/module, and in different orders, and by different components/modules, yet still achieve the functions of the computing device 1200 and model-related manager 1222.

In addition, programming interfaces to the data stored as part of the computing device 1200 and model-related manager 1222, can be available by standard mechanisms such as through C, C++, C#, and Java APIs; libraries for accessing files, databases, or other data repositories; scripting languages such as XML; or Web servers, FTP servers, NFS file servers, or other types of servers providing access to stored data. The model-related data storage 1216 and data repository 1220 may be implemented as one or more database systems, file systems, or any other technique for storing such information, or any combination of the above, including implementations using distributed computing techniques.

Different configurations and locations of programs and data are contemplated for use with techniques described herein. A variety of distributed computing techniques are appropriate for implementing the components of the illustrated embodiments in a distributed manner including but not limited to TCP/IP sockets, RPC, RMI, HTTP, and Web Services (XML-RPC, JAX-RPC, SOAP, and the like). Other variations are possible. Other functionality could also be provided by each component/module, or existing functionality could be distributed amongst the components/modules in different ways, yet still achieve the functions of the model-related manager 1222.

Furthermore, in some embodiments, some or all of the components of the computing device 1200 and model-related manager 1222 may be implemented or provided in other manners, such as at least partially in firmware or hardware, including, but not limited to one or more application-specific integrated circuits ("ASICs"), standard integrated circuits, controllers (e.g., by executing appropriate instructions, and including microcontrollers or embedded controllers), field-programmable gate arrays ("FPGAs"), complex programmable logic devices ("CPLDs"), and the like. Some or all of the system components or data structures may also be stored as contents (e.g., as executable or other machine-readable software instructions or structured data) on a computer-readable medium (e.g., as a hard disk; a memory; a computer network, cellular wireless network or other data transmission medium; or a portable media article to be read by an appropriate drive or via an appropriate connection, such as a DVD or flash memory device) so as to enable or configure the computer-readable medium or one or more associated computing systems or devices to execute or otherwise use, or provide the contents to perform, at least some of the described techniques.

The various embodiments described above can be combined to provide further embodiments. All of the U.S. patents, U.S. patent application publications, U.S. patent applications, foreign patents, foreign patent applications and non-patent publications referred to in this specification or listed in the Application Data Sheet are incorporated herein by reference, in their entirety. In cases where the present patent application conflicts with an application or other document incorporated herein by reference, the present application controls. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A computer-implemented method for imputing a value associated with a subject within an electronic health record (EHR) system, the method comprising:

- receiving, by a computing device and from a second computing device, a request to impute the value associated with the subject at a temporal instance;
- retrieving, by the computing device, a subset of data associated with the subject from the EHR system, the subset of data comprising a plurality of stored values associated with one or more temporal instances;
- providing, by the computing device, the temporal instance indicated in the request and the subset of data to a trained artificial intelligence engine, the trained artificial intelligence engine configured to perform actions, comprising:
  - determining, by the computing device, relationships between the stored values by:
    - calculating a set of scores for multiple subsets of features of the stored values, wherein the set of scores represents interdependencies between the stored values;
  - determining, by the computing device, time weights based on a temporal proximity of the one or more temporal instances of the stored values relative to the temporal instance of the value being imputed;
  - adjusting, by the computing device, the calculated scores based on the time weights to generate time-adjusted scores;
  - generating, by the computing device, an imputed value based on a combination of the stored values and the time-adjusted scores, wherein the imputed value corresponds to at least one lab test value;
  - providing, by the computing device, the imputed value to the second computing device in response to the request;
  - generating, by the computing device, one or more visualizations that include a heatmap indicating different predictive relevance of a plurality of values including the imputed value; and
  - displaying, by the computing device, one or more predicted health conditions for the subject based on the one or more visualizations.

2. The method of claim 1, wherein the subset of data are associated with the subject.

3. The method of claim 1, wherein the request includes a unit of measure.

4. The method of claim 1, wherein determining the time weights based on the temporal proximity of the one or more temporal instances of the stored values relative to the temporal instance of the value being imputed comprises applying a time decay function to the calculated scores that is dependent on differences between the temporal instance of the value being imputed and the one or more temporal instances of the stored values in the EHR.

5. The method of claim 4, wherein the time decay function comprises an exponential time decay function or a linear time decay function.

6. The method of claim 1, wherein adjusting the calculated scores based on the time weights comprises applying more weight to stored values that are relatively nearer in time to the temporal instance of the value being imputed.

7. The method of claim 1, wherein determining the relationships between the stored values in the EHR comprises use of a multi-head attention module.

8. The method of claim 1, wherein generating the imputed value includes:

- applying a weight matrix to the time-adjusted scores to combine them into a single representation; and
- processing the single representation using a classifier to generate the imputed value.

9. The method of claim 8, wherein applying the weight matrix to the time-adjusted scores comprises using a Hadamard product module.

10. The method of claim 8, wherein processing the single representation to generate the imputed value comprises using a multilayer perceptron module.

11. The method of claim 1, further comprising predicting an occurrence of an adverse event based on the imputed value.

12. The method of claim 1, further comprising assessing a predicted eligibility for a clinical trial based on the imputed value.

13. The method of claim 1, further comprising predicting a gap in care based on the imputed value.

14. The method of claim 1, wherein the stored values include at least one prior lab test result.

15. The method of claim 1, wherein the stored values include at least one prior clinical assessment result.

16. The method of claim 1, wherein the temporal instance of the value being imputed comprises a date.

17. A computing system for imputing a value associated with a subject within a structured electronic health record (EHR) system, the computing system comprising:

one or more processors; and one or more non-transitory computer-readable media collectively storing instructions that, when collectively executed by the one or more processors, cause the one or more processors to perform actions, the actions comprising:

receiving a request to impute the value associated with the subject at a temporal instance;

retrieving a subset of data associated with the subject from the EHR system, the subset of data comprising a plurality of stored values associated with one or more temporal instances;

providing the temporal instance indicated in the request and the subset of data to a trained artificial intelligence engine, the trained artificial intelligence engine configured to perform actions, comprising:

determining relationships between the stored values by:

calculating a set of scores for multiple subsets of features of the stored values, wherein the set of scores represents interdependencies between the stored values;

determining time weights based on a temporal proximity of the one or more temporal instances of the stored values relative to temporal instance of the value being imputed;

adjusting the calculated scores based on the time weights to generate time-adjusted scores;

generating an imputed value based on a combination of the stored values and the time-adjusted scores, wherein the imputed value corresponds to at least one lab test value;

providing the imputed value in response to the request;

generating one or more visualizations that include different shadings indicating different predictive relevance of a plurality of values including the imputed value; and presenting one or more predicted health conditions for the subject based on the one or more visualizations.

18. One or more non-transitory computer readable media collectively storing a computer program thereon, the program, when collectively executed by one or more processors, implements operations for imputing a value associated with a subject within a structured electronic health record (EHR) system, the operations comprising:

receiving a request to impute the value associated with the subject at a temporal instance;

retrieving a subset of data associated with the subject from the EHR system, the subset of data comprising a plurality of stored values associated with one or more temporal instances;

providing the temporal instance indicated in the request and the subset of data to a trained artificial intelligence engine, the trained artificial intelligence engine configured to perform actions, comprising:

determining relationships between the stored values by:

calculating a set of scores for multiple subsets of features of the stored values, wherein the set of scores represents interdependencies between the stored values;

determining time weights based on a temporal proximity of the one or more temporal instances of the stored values relative to the temporal instance of the value being imputed;

adjusting the calculated scores based on the time weights to generate time-adjusted scores;

generating an imputed value based on a combination of the stored values and the time-adjusted scores, wherein the imputed value corresponds to at least one lab test value;

providing the imputed value in response to the request;

generating one or more visualizations that include different colors indicating different predictive relevance of a plurality of values including the imputed value; and causing presentation of one or more predicted health conditions for the subject based on the one or more visualizations.

* * * * *